United States Patent
Zahn et al.

(10) Patent No.: US 11,922,164 B2
(45) Date of Patent: Mar. 5, 2024

(54) SYSTEM AND METHOD FOR SENSORY CHARACTERIZATION

(71) Applicant: Climax Foods Inc., Berkeley, CA (US)

(72) Inventors: Oliver Zahn, Berkeley, CA (US); Karthik Sekar, Berkeley, CA (US); Richard Gerkin, Berkeley, CA (US)

(73) Assignee: Climax Foods Inc., Berkeley, CA (US)

( * ) Notice: Subject to any disclaimer, the term of this patent is extended or adjusted under 35 U.S.C. 154(b) by 0 days.

(21) Appl. No.: 18/107,294

(22) Filed: Feb. 8, 2023

(65) Prior Publication Data

US 2023/0259363 A1 Aug. 17, 2023

Related U.S. Application Data

(60) Provisional application No. 63/320,635, filed on Mar. 16, 2022, provisional application No. 63/311,739, filed on Feb. 18, 2022, provisional application No. 63/308,465, filed on Feb. 9, 2022.

(51) Int. Cl.
| | |
|---|---|
| *G06F 9/06* | (2006.01) |
| *G01N 33/00* | (2006.01) |
| *G01N 33/02* | (2006.01) |
| *G06N 20/00* | (2019.01) |
| *G16C 20/70* | (2019.01) |

(52) U.S. Cl.
CPC ........... *G06F 9/06* (2013.01); *G01N 33/0001* (2013.01); *G01N 33/02* (2013.01); *G06N 20/00* (2019.01); *G16C 20/70* (2019.02)

(58) Field of Classification Search
None
See application file for complete search history.

(56) References Cited

U.S. PATENT DOCUMENTS

| | | | |
|---|---|---|---|
| 9,891,201 B2* | 2/2018 | Hort | G01N 33/02 |
| 10,915,818 B1 | 2/2021 | Patel et al. | |
| 10,957,424 B1 | 3/2021 | Navon et al. | |
| 10,962,473 B1 | 3/2021 | O'Hara et al. | |
| 10,970,621 B1 | 4/2021 | Pichara et al. | |
| 10,993,465 B2 | 5/2021 | Pichara et al. | |
| 11,164,069 B1 | 11/2021 | Korsunsky et al. | |
| 11,164,478 B2 | 11/2021 | Pichara et al. | |
| 11,205,101 B1 | 12/2021 | Kawas Garcia et al. | |
| 11,348,664 B1 | 5/2022 | Kaneko et al. | |
| 11,373,107 B1 | 6/2022 | Clavero et al. | |

(Continued)

FOREIGN PATENT DOCUMENTS

WO 2021240474 A1 12/2021

OTHER PUBLICATIONS

Day, Adrienne, "How one man's philosophy of data and food science could help save the planet", Grist.org, Nov. 10, 2020.

(Continued)

*Primary Examiner* — Daniel S Larkin
(74) *Attorney, Agent, or Firm* — Jeffrey Schox; Diana Lin

(57) ABSTRACT

In variants, a method for sensory characterization can include: determining attributes for a sample, collecting sensory data for the sample, determining a sensory characterization model, training the sensory characterization model based on the attributes and the sensory data, determining attributes for a test sample, and predicting a sensory characterization for the test sample using the sensory characterization model.

9 Claims, 22 Drawing Sheets

(56) References Cited

U.S. PATENT DOCUMENTS

| | | |
|---|---|---|
| 11,404,144 B1 | 8/2022 | Kang et al. |
| 2012/0027897 A1 | 2/2012 | Innocenzi |
| 2014/0038850 A1 | 2/2014 | Fasan et al. |
| 2016/0165935 A1 | 6/2016 | Eddy et al. |
| 2017/0330097 A1 | 11/2017 | Chae et al. |
| 2018/0279632 A1 | 10/2018 | Stryker et al. |
| 2019/0369073 A1 | 12/2019 | Gafsou |
| 2021/0219583 A1 | 7/2021 | Pichara et al. |

OTHER PUBLICATIONS

Ravia, Aharon, et al., "A measure of smell enables the creation of olfactory metamers", Nature, published Nov. 11, 2020, https://doi.org/10.1038/s41586-020-2891-7.

Shiebar, Jonathan, "Founded by an Impossible Foods and Google data scientist, Climax Foods raises $7.5 million to tackle the cheesiest market", Techcrunch, Sep. 1, 2020.

Snitz, Kobi, "Predicting Odor Perceptual Similarity from Odor Structure", PLOS Computational Biology, Sep. 2013, vol. 9, Issue 9.

Watson, Elaine, "Climax Foods raises $7.5m: 'We want to replace animals as inefficient factories for converting plants into meat and dairy'", FoodNavigator-usa.com, Sep. 2, 2020.

\* cited by examiner

SYSTEM AND METHOD FOR SENSORY CHARACTERIZATION

CROSS-REFERENCE TO RELATED APPLICATIONS

This application claims the benefit of U.S. Provisional Application No. 63/308,465 filed 9 Feb. 2022, U.S. Provisional Application No. 63/311,739 filed 18 Feb. 2022, and U.S. Provisional Application No. 63/320,635 filed 16 Mar. 2022, each of which is incorporated in its entirety by this reference.

TECHNICAL FIELD

This invention relates generally to the sensory field, and more specifically to a new and useful system and method in the sensory field.

DETAILED DESCRIPTION

The following description of the embodiments of the invention is not intended to limit the invention to these embodiments, but rather to enable any person skilled in the art to make and use this invention.

1. Overview

Figure 1:
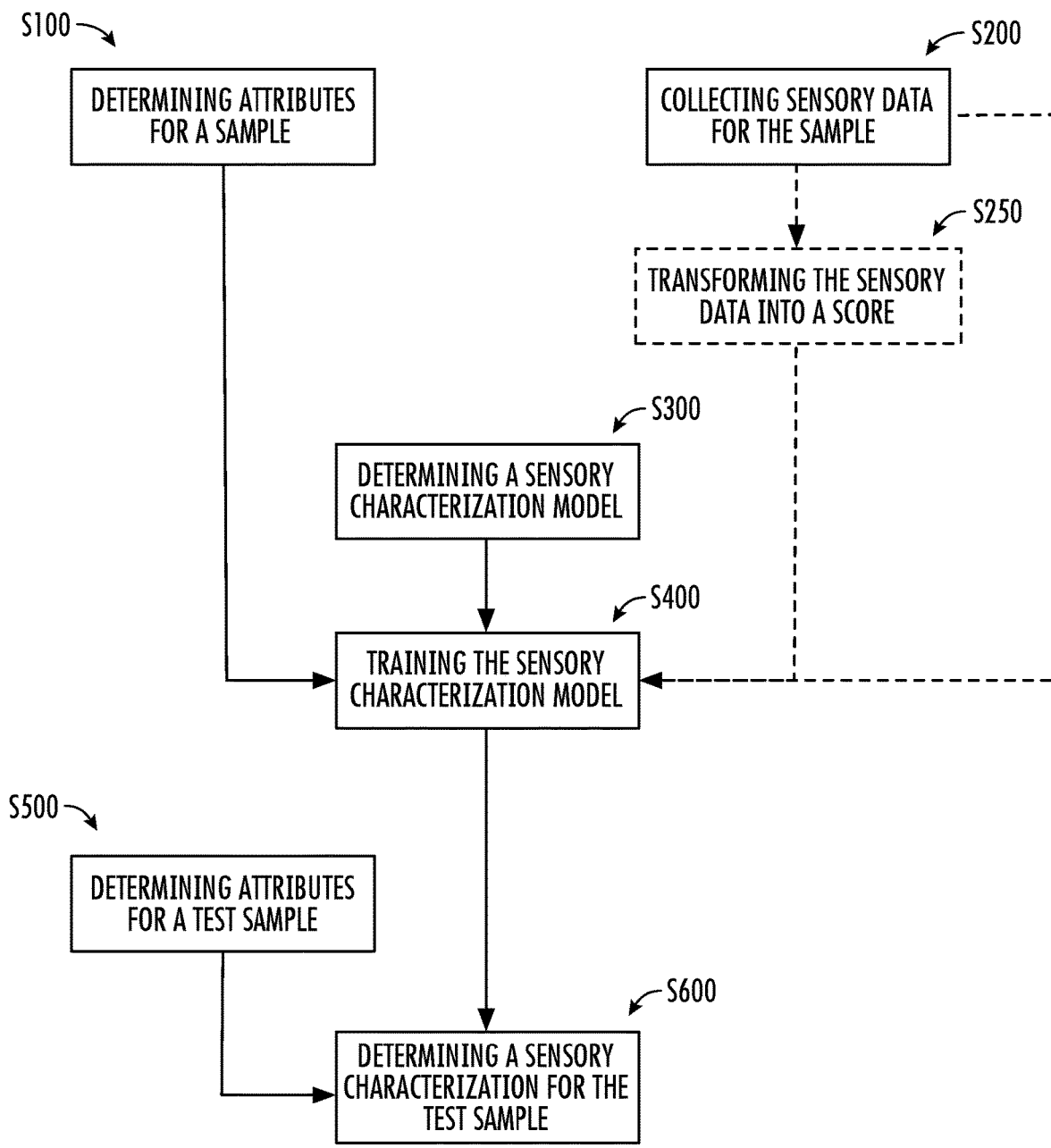
FIG. 1 is a schematic representation of a variant of the method.

As shown in FIG. 1, the method can include: determining attributes for a sample S100, collecting sensory data for the sample S200, and determining a sensory characterization model S300. The method can additionally or alternatively include determining attributes for a test sample S500 and determining a sensory characterization for the test sample S600.

In variants, the method can function to predict a sensory characterization (e.g., flavor characterization) of a test sample, to predict a sensory similarity between two samples, to predict attributes for a test sample (e.g., attributes associated with the olfactory receptor composition and/or gustation composition, attributes with a high impact on the test sample sensory characterization, attributes resulting in a target sensory characterization, etc.), determine the components contributing to a sensory characteristic (e.g., flavor), determine a set of components that would result in a target sensory characteristic, and/or provide other functionalities.

2. Examples

In an example, the method can include: selecting a set of samples, collecting sample comparison data by ranking the samples according to the relative perceived sensory intensities (e.g., using a human panel), and optionally transforming the comparison data into a sensory intensity score for each sample (e.g., a probability of a given ranking, a similarity score, a score using a rating system such as ELO or a Plackett-Luce model, etc.). The samples can be food samples, volatile fractions (e.g., of the food samples), and/or be any other sample. The sensory intensity score can be for a given sensory quality (e.g., a set of sensory intensity scores for each sensory quality), for a set of sensory qualities, and/or be an overall intensity score, and can be the raw score output by the rating system or be normalized to another scale. The perceived sensory intensity can be a gustation intensity, orthonasal intensity, retronasal intensity, and/or other intensity. The method can additionally include determining (e.g., measuring) attributes or features of a sample, such as the sample's chemical composition (e.g., chemical components and respective concentrations) and/or the sample's context (e.g., matrix size, matrix composition, human sensory panelist, etc.). The chemical composition can be measured for one or more volumes, such as a vial headspace, breath (e.g., pre- or post-mastication), orthonasal bulb, retronasal cavity, or other volume. A sensory characterization model can then be trained to predict a sensory intensity score (e.g., a probability of a given ranking relative to another sample; a curve describing the sensory intensity), given the respective sample's attribute values.

After the sensory characterization model has been trained, it can be used to predict the sensory intensity score of a test sample (e.g., an overall intensity or the intensity of each of a set of qualities). The test sample can be a physical sample (e.g., with measured attributes), an in silico sample (e.g., with predicted attributes), and/or be any other sample. The predicted sensory characterization can be used to: determine a sensory characteristic (e.g., flavor intensity) for the sample, determine a sensory similarity between two samples (e.g., a prototype sample and a target sample), determine which intervention (e.g., ingredient change, process parameter change, etc.) to apply in the next sample preparation cycle (e.g., using Bayesian optimization, based on the sensory similarity, etc.), and/or otherwise used.

In an illustrative example, all or a portion of the method can be first performed for single-component samples (e.g., pure molecules diluted to a test concentration and/or a test perceived sensory intensity), and then performed for multi-component (e.g., mixture) samples. In this example, one or more models can be trained: a component model can be determined to predict component sensory characterizations, and a mixture model can be trained to predict the mixture sensory characterization based on the component sensory intensity characterizations; a single model can be trained to directly predict the mixtures' sensory characterization (e.g., based on the components' attributes); a single model can be first trained to predict single-component sensory characterizations, then subsequently trained to predict a mixture sensory characterization; and/or any other model can be trained.

3. Technical Advantages

Variants of the technology can confer one or more advantages over conventional technologies.

First, conventionally, the flavors and/or other sensory characteristics of a sample are characterized by human panelists, who score each sample along a predefined scale. Unfortunately, because this method is largely subjective, conventional methods suffer from inaccuracy due to variability in scale usage between human panelists, inter-sample fatigue, anchoring effects, and complex component sensory characteristic interactions in mixtures, amongst other issues. Also, because sensory characteristics vary by concentration, conventional methods required individual scores for each compound-concentration permutation—this required large amounts of human panel data to reduce uncertainty in flavor profiles and/or other sensory characterizations. Further, because compound sensory characteristic interactions are nonlinear and vary drastically, scores assigned for constituent compounds within a mixture cannot be reliably used to determine scores for the overall mixture—new human panelist data must be collected.

Variants of the method can mitigate these issues by ranking the perceived sensory intensity instead of using conventional scales (e.g., instead of determining absolute intensity scores). Data collected from human panelists making direct comparisons between two or more samples (e.g., ranking the samples based on perceived sensory intensity, rating the quality of a single attribute, comparing the samples in terms of sensory similarity, etc.) can be far more consistent across panelists than data collected from the same panelists scoring the samples using conventional scales. Thus, ranking the perceived sensory intensity can enable a given reduction in uncertainty to be reached with fewer datapoints by (at least in part) mitigating perceptual noise associated with quantitative rankings. Additionally, in variants, computational load can be further reduced by limiting the model to a subset of molecules under consideration.

Second, in variants of the technology, the inventors have discovered that the context of a sample (e.g., substrate, phase, matrix, human panelist, etc.) can influence the perceived sensory intensity and/or sensory qualities of the sample. By incorporating the context into model training and/or as an additional model, the sensory characterization model can have increased accuracy.

Third, the inventors have discovered that the composition of a sample present in the olfactory receptor (e.g., olfactory receptor composition) and/or on the tongue (e.g., gustation composition) after a human smells and/or masticates the sample can vary significantly from the composition of the sample headspace. Additionally, the inventors have discovered that the olfactory receptor composition and/or gustation composition can be more predictive of the perceived flavor characteristics (e.g., flavor intensity and/or flavor quality) relative to the vial headspace composition. In variants, the olfactory receptor composition and/or the gustation composition for a sample can be predicted based on the vial headspace composition, sample context information (e.g., process parameters, sample matrix, etc.), and/or other sample attributes. Additionally or alternatively, the olfactory intensity or gustation intensity for a sample can be predicted based on the vial headspace composition, sample context information, and/or other sample attributes. The predicted olfactory receptor composition and/or gustation composition can optionally be used to predict a sensory characterization for the sample.

However, further advantages can be provided by the system and method disclosed herein.

4. Method

As shown in FIG. 1, the method can include: determining attributes for a sample S100, collecting sensory data for the sample S200, determining a sensory characterization model S300, determining attributes for a test sample S500, and determining a sensory characterization for the test sample S600.

All or portions of the method can be performed once (e.g., for one or more samples, for one or more sample components, for one or more sensory qualities, for one or more sensory characteristics, for one or more sensory panelists, etc.), iteratively (e.g., for each of a set of samples, for each of a set of sample components, for each of a set of sensory qualities, for each of a set of sensory characteristics, for each of a set of sensory panelists, etc.), multiple times (e.g., to generate a database of sample sensory data, to generate a database of sample sensory characterizations, etc.), in real time (e.g., responsive to a request), asynchronously, periodically, and/or at any other suitable time. All or portions of the method can be performed automatically, manually, semi-automatically, and/or otherwise performed.

All or portions of the method can be performed by a computing system, using a database (e.g., a system database, a third-party database, etc.), using assays and/or assay tools (e.g., to determine sample attributes, to determine a sensory characterization, etc.), by a user, and/or by any other suitable system. The computing system can include one or more: CPUs, GPUs, custom FPGA/ASICS, microprocessors, servers, cloud computing, and/or any other suitable components. The computing system can be local, remote, distributed, or otherwise arranged relative to any other system or module.

Figure 15A:
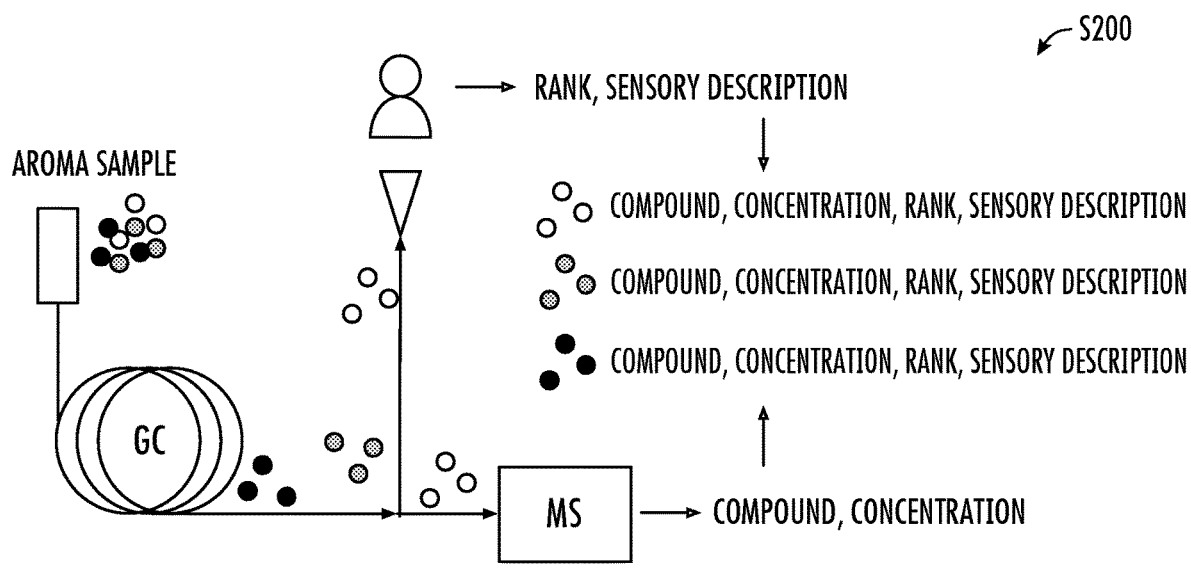
FIG. 15A depicts an illustrative example of a GCMS system wherein components are analyzed on an individual basis.
Figure 15B:
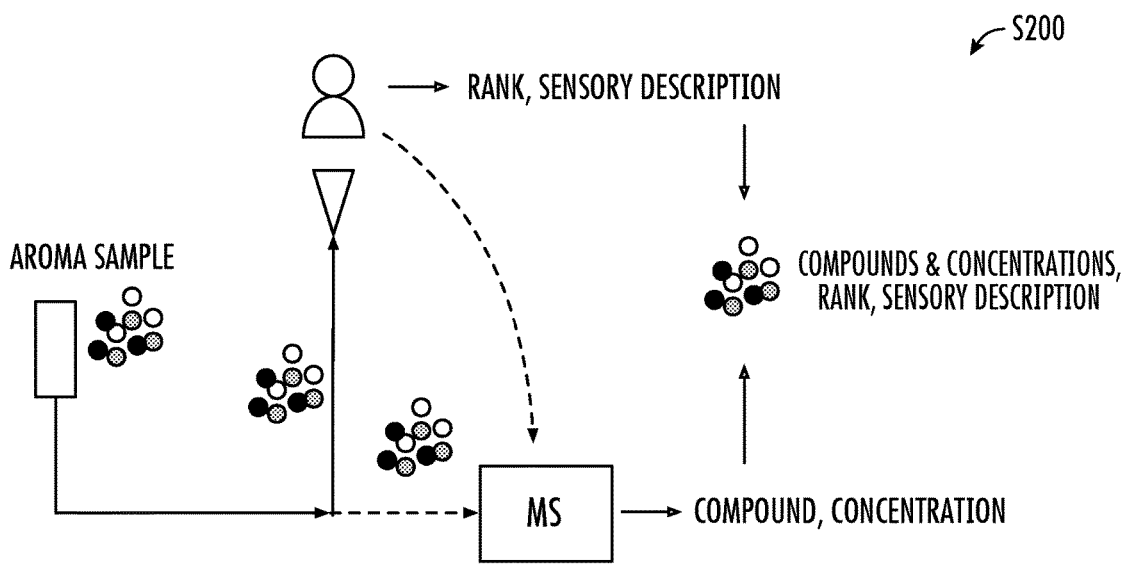
FIG. 15B depicts an illustrative example of a measurement system wherein the sample is analyzed as a whole.

Examples of assays and/or assay tools that can be used include: a differential scanning calorimeter, Schreiber Test, an oven, a water bath, a texture analyzer, a rheometer, spectrophotometer, centrifuge, moisture analyzer, light microscope, atomic force microscope, confocal microscope, laser diffraction particle size analyzer, polyacrylamide gel electrophoresis system, mass spectrometry (MS), time-of-flight mass spectrometry (TOF-MS), gas chromatography (GC), gas chromatography-olfactometry (GCO), gas chromatography-mass spectrometry (GC-MS; example shown in FIG. 15A), selected ion flow tube mass spectrometry (SIFT-MS), liquid chromatography (LC), liquid chromatography-mass spectrometry (LC-MS), fast protein LC, high-performance liquid chromatography (HPLC), enzymatic assays, protein concentration assay systems, thermal gravimetric analysis system, thermal shift, ion chromatography, dynamic light scattering system, Zetasizer, protein concentration assays (e.g., Q-bit, Bradford, Biuret, Lecco, etc.), particle size analyzer, sensory panels (e.g., to collect sensory data), capillary electrophoresis SDS, spectroscopy, absorbance spectroscopy, CE-IEF, total protein quantification, high temperature gelation, microbial cloning, Turbiscan, stereospecific analysis, olfactometers, electrophysiological testing (e.g., of the panelist, such as EEG, etc.), psychophysical testing (e.g., of the panelist), and/or any other assay and/or assay tool.

Determining attributes for a sample S100 functions to generate training data for the sensory characterization model, to generate training data for the attribute prediction model, to generate data for sensory characterization of a sample (e.g., inputs for the sensory characterization model), and/or to determine information which can influence sensory characteristics (e.g., for a given sample component, for a sample overall, etc.). S100 can be performed before, during, and/or after manufacturing the sample; after mastication; after sample reaction (e.g., lysing, metabolism, etc.); prior to S200; during S200; and/or any other time. The sample can be a single component and/or a mixture of components. A component can be a molecule, compound, ingredient, isolate, and/or otherwise defined. Single-component samples (e.g., standards) may contain impurities, wherein the amount of impurities can be known (e.g., measured) or unknown. One or more components can optionally be diluted (e.g., in an odorless solvent) to a target sensory intensity (e.g., a target perceived sensory intensity), a target concentration, and/or any other target. One or more components can optionally be added to or be within a matrix (e.g., wherein the sample includes or does not include the matrix). The matrix can be a solid matrix, semi-solid matrix, and/or or any other matrix. Examples of matrices include a food product intermediate, material, gel, solution, and/or any other substrate.

The sample can be a solid, liquid (e.g., oil, aqueous solution, etc.), gas, and/or have any other suitable phase. The sample can be a substrate (e.g., food product, food product intermediate, material, gel, solution, etc.) and/or extracted from a substrate.

The substrate can optionally be a food product and/or be used to manufacture a food product. For example, the substrate can be: a replacement (e.g., analog) for a target food product (e.g., the substrate can be a plant-based analog for an animal food product), used to manufacture a target food product, a food product with target characteristics, and/or any other food product. The substrate can be a vegan product, a food product without animal products and/or with less animal products (e.g., relative to a target animal product), a plant-based food product, a microbial-based food product, a nonmammalian-based food product, and/or any other food product. Examples of target food products include: dairy fats (e.g., ghee, other bovine milk fats, etc.), milk, curds, cheese (e.g., hard cheese, soft cheese, semi-hard cheese, semi-soft cheese), butter, yogurt, cream cheese, dried milk powder, cream, whipped cream, ice cream, coffee cream, other dairy products, egg products (e.g., scrambled eggs), additive ingredients, mammalian meat products (e.g., ground meat, steaks, chops, bones, deli meats, sausages, etc.), fish meat products (e.g., fish steaks, filets, etc.), any animal product, and/or any other suitable food product. In specific examples, the target food product includes mozzarella, burrata, feta, brie, ricotta, camembert, chevre, cottage cheese, cheddar, parmigiano, pecorino, gruyere, edam, gouda, jarlsberg, and/or any other cheese.

The sample can optionally be extracted from the solid fraction, liquid fraction, and/or gaseous fraction (e.g., gaseous headspace) of the substrate; from a human subject (e.g., the nasal cavity, the mouth, etc.), and/or from any other source. The substrate can be unprocessed and/or preprocessed before determining the sample attributes. A preprocessed substrate can include a substrate subjected to a chemical reaction, a substrate that is masticated (e.g., by a human, by a machine, etc.), and/or a substrate subjected to any other processing prior to attribute determination. Preprocessing can be performed to measure components which can influence different types of sensory characteristics (e.g., retronasal olfaction, orthonasal olfaction, taste, gustation, etc.). In a first example, a human subject chews a substrate and then breathes into a device (e.g., out the nose, out the mouth, etc.) to measure attributes of the breath sample (e.g., to determine olfactory receptor attributes and/or gustation attributes). In a second example, a substrate is unprocessed and the components of the gaseous headspace of the substrate are measured (e.g., to determine headspace attributes). However, the substrate can be otherwise processed.

The sample can be associated with a set of sample attributes, including: composition, context, molecular structure (e.g., for the sample, for one or more sample components, for each sample component in a mixture, etc.), and/or any other sample information.

The sample composition can include the identity and/or amounts of the components in the sample. A component can be a substance, molecule, compound, impurity, microbe, and/or otherwise defined. Examples of sample composition include: molar fraction, volume fraction, mass fraction, molality, molarity, mixing ratio, and/or any other component information. The amount of the component can be: the component concentration, the percentage of the overall sample that the component represents, the mass of the component within the sample, the component volume, and/or any other suitable measure of the component amount. The sample composition can optionally be a headspace composition (e.g., composition of the gaseous fraction of the substrate), an olfactory receptor composition (e.g., composition of a fraction of the substrate present in or on the olfactory receptor, the olfactory bulb, and/or the nasal cavity before, during, and/or after mastication), a gustation composition (e.g., composition of a fraction of the substrate present on the tongue before, during, and/or after mastication), and/or any other composition associated with the sample. The composition can be for all components of the sample and/or for a subset of components of the sample (e.g., a single component, a set of components of interest, etc.). In a first example, the components of interest include components that are representative of a target food product (e.g., blue cheese) and/or food category (e.g., cheese, dairy, etc.). In a second example, the components of interest include compounds not found in a target food product (e.g., which may be found in the sample; which may negatively and/or positively impact sensory characteristics; which are found in similar samples, etc.). In a third example, the components of interest include components with a high impact on sensory characteristics (e.g., determined using explainability and/or interpretability methods).

The sample context can include sample phase, sample matrix attributes (e.g., matrix identifier, matrix functional properties, matrix composition, matrix structure, matrix density, matrix porosity, matrix fibrosity, matrix size, etc.), substrate attributes (e.g., substrate functional properties, substrate structure, etc.), process parameters, environmental parameters (e.g., while collecting sensory data, while measuring attributes, etc.), sensory panelist attributes (e.g., identifier for a sensory panelist associated with sensory data collection), metabolic pathways (e.g., available metabolic pathways determined based on sample composition, microbial cultures and/or other ingredients, other process parameters, etc.), other components in other phases or fractions (e.g., trapped in the solid phase or liquid phase), nutritional profile (e.g., macronutrient profile, micronutrient profile, etc.), texture (e.g., texture profile, firmness, toughness, puncture, stretch, compression response, mouthfeel, viscosity, graininess, relaxation, stickiness, chalkiness, flouriness, astringency, crumbliness, stickiness, stretchiness, tearability, mouth melt, etc.), solubility, melt profile, smoke profile, gelation point, precipitation, stability (e.g., room temperature stability), emulsion stability, ion binding capacity, heat capacity, solid fat content, chemical properties (e.g., pH, affinity, surface charge, isoelectric point, hydrophobicity/hydrophilicity, chain lengths, chemical composition, nitrogen levels, chirality, stereospecific position, etc.), physiochemical properties, denaturation point, denaturation behavior, aggregation point, aggregation behavior, particle size, structure (e.g., microstructure, macrostructure, fat crystalline structure, etc.), folding state, folding kinetics, interactions with other molecules (e.g., dextrinization, caramelization, coagulation, shortening, interactions between fat and protein, interactions with water, aggregation, micellization, etc.), fat leakage, water holding and/or binding capacity, fat holding and/or binding capacity, fatty acid composition (e.g., percent saturated/unsaturated fats), moisture level, turbidity, properties determined using an assay tool, and/or any other sample information (e.g., associated or unassociated with sensory characteristics). The sample context can be for the substrate, for the sample, for one or more sample components, and/or be otherwise defined.

Environmental parameters can be conditions associated with attribute measurements (e.g., conditions the sample was exposed to during attribute measurements), sensory data collection (e.g., conditions the sample and/or sensory panelist was exposed to during sensory data collection), and/or other conditions. Examples of environmental parameters can include: time (e.g., time of day), temperature, humidity, sample testing sequence (e.g., the most recent sample smelled by the sensory panelist prior to smelling the sample of interest), and/or any other conditions.

Process parameters are preferably specifications prescribing the manufacturing of the sample (e.g., a recipe), but can be otherwise defined. Process parameters can define: manufacturing specifications; the amounts thereof (e.g., ratios, volume, concentration, mass, etc.); temporal parameters thereof (e.g., when the input should be applied, duration of input application, etc.); and/or any other suitable manufacturing parameter. Manufacturing specifications can include: ingredients, treatments, and/or any other sample manufacturing input, wherein the process parameters can include parameters for each specification. Examples of treatments can include: adjusting temperature, adjusting salt level, adjusting pH level, diluting, pressurizing, depressurizing, humidifying, dehumidifying, agitating, resting, adding ingredients, removing components (e.g., filtering, draining, centrifugation, etc.), adjusting oxygen level, brining, comminuting, fermenting, mixing (e.g., homogenizing), gelling (e.g., curdling), and/or other treatments. Examples of treatment parameters can include: treatment type, treatment duration, treatment rate (e.g., flow rate, agitation rate, cooling rate, rotor stator rpm, etc.), treatment temperature, time (e.g., when a treatment is applied, when the sample is characterized, etc.), and/or any other parameters.

Examples of ingredients can include: plant matter, proteins (e.g., protein isolates), a lipid component (e.g., fats, oils, etc.), an aqueous component (e.g., water, a sucrose solution, etc.), preservatives, acids and/or bases, macronutrients (e.g., protein, fat, starch, sugar, etc.), nutrients, micronutrients, carbohydrates (e.g., sugars, starches, fibers, polysaccharides, such as maltodextrin, gums, etc.), vitamins, enzymes (e.g., transglutaminase, chymosin, tyrosinase, bromelain, papain, ficain, other cysteine endopeptidases, rennet enzymes and/or rennet-type enzymes, etc.), emulsifiers (e.g., lecithin), particulates, hydrocolloids (e.g., thickening agents, gelling agents, emulsifying agents, stabilizers, etc; such as starch, gelatin, pectin, and gums, such as agar, alginic acid, sodium alginate, guar gum, locust bean gum, beta-glucan, xanthan gum, etc.), salts (e.g., NaOH, NaCl, CaCl2, KCl, NaI, MgCl2, etc.), minerals (e.g., calcium), chemical crosslinkers (e.g., transglutaminase) and/or non-crosslinkers (e.g., L-cysteine), coloring, flavoring compounds, vinegar (e.g., white vinegar), mold powders, microbial cultures, carbon sources (e.g., to supplement fermentation), calcium citrate, any combination thereof, and/or any other ingredient. The ingredients can optionally exclude and/or include less than a threshold amount (e.g., 10%, 5%, 3%, 3%, 1%, 0.5%, 0.1%, etc.) of added: animal products, animal-derived ingredients, gums (e.g., polysaccharide thickeners), hydrocolloids, allergens, phospholipids, and/or any other suitable ingredient. The ingredients are preferably food-safe, but can alternatively be not food-safe. The ingredients can be whole ingredients (e.g., include processed plant material), ingredients derived from plant-based sources, ingredients derived from plant genes, synthetic ingredients, and/or be any other ingredient.

In a first variant, determining sample attributes includes measuring attributes of the sample. Alternatively, the sample attributes can remain unmeasured. Sample attributes can be measured using GC-MS, SIFT-MS, HPLC, LC-MS, enzymatic assays, and/or other assays or assay tools. In a first example, the composition of a breath sample expelled via a human nose and/or mouth (e.g., after masticating or eating the sample substrate) is measured. In this example, a fixture (e.g., a nasal attachment coupled to the nose of a sensory panelist and/or positioned under the nose of a sensory panelist) can be mounted to a GC-MS, SIFT-MS, and/or any other measurement tool to collect the breath expulsion sample components. Additionally or alternatively, a sensory panelist can forcibly expel air via their nostrils such that the measurement tool can collect the breath expulsion sample components (e.g., without using a nasal fixture). In a first specific example, an olfactory receptor composition can include the composition of a breath sample expelled via a human nose. In a first specific example, a gustation composition can include the composition of a breath sample expelled via a human mouth. In a second example, the composition of saliva (e.g., after masticating or eating the sample substrate) is measured. In a specific example, a gustation composition can include the composition of saliva. In a third example, the attributes of a headspace of a substrate (e.g., vial headspace) are measured. In a fourth example, the sample attributes are measured from the solid phase of a substrate (e.g., matrix attributes measured with microscopy tools). In a fifth example, values for the sample context can be measured (e.g., measuring a matrix attribute, measuring an environmental parameter during sensory data collection). In a sixth example, the molecular structure for one or more sample components can be measured (e.g., using a microscopy tool). However, sample attributes can be measured from any phase and/or combination of phases using any measurement methodology.

In a second variant, the sample attributes can be retrieved and/or predetermined. For example, process parameters, matrix attributes, sensory panelist attributes, environmental parameters, molecular structures, and/or any other sample attributes can be retrieved from a database (wherein the database includes an association between an identifier for the sample and the corresponding the sample attributes). In a first illustrative example, a sample context includes the manufacturing step of raising the temperature to 100 degrees Fahrenheit. In a second illustrative example, a sample context includes the preprocessing step of masticating the substrate. In a third illustrative example, the sample context includes a quantitative context value determined based on a collection of process parameters.

Figure 16A:
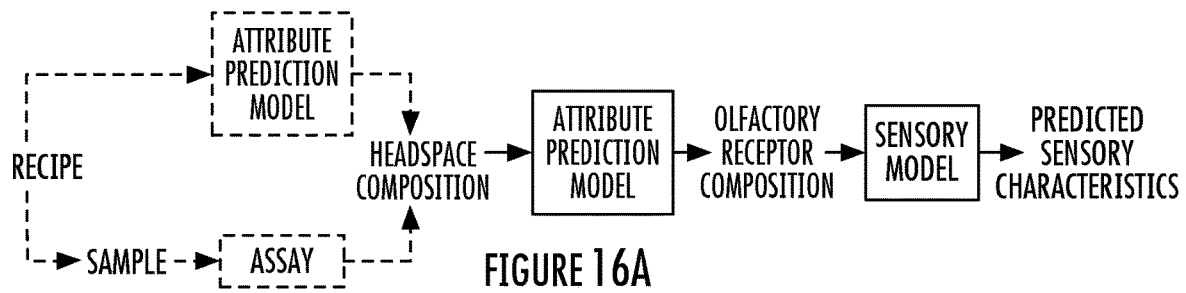
FIG. 16A depicts a first example of predicting sensory characteristics based on predicted olfactory receptor composition.
Figure 16B:
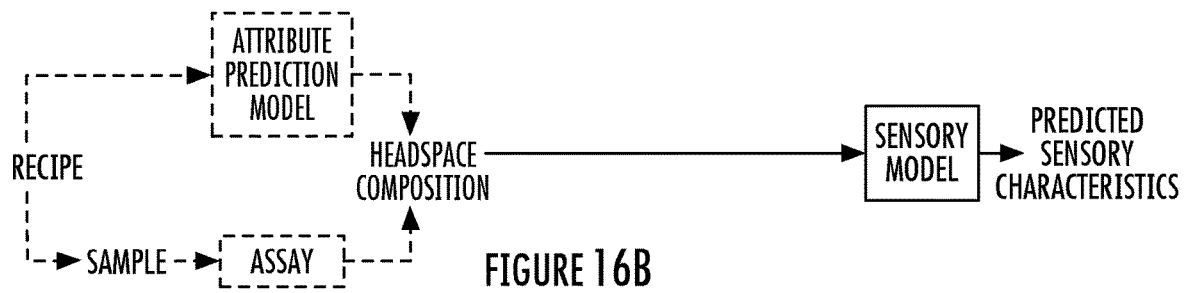
FIG. 16B depicts an example of predicting sensory characteristics based on headspace composition.
Figure 16C:
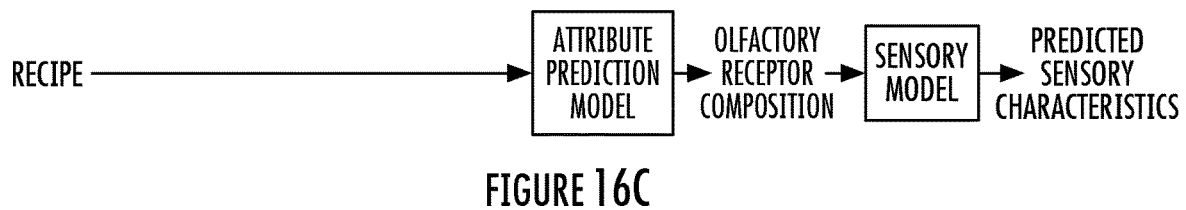
FIG. 16C depicts a second example of predicting sensory characteristics based on predicted olfactory receptor composition.
Figure 16D:
FIG. 16D depicts an example of predicting sensory characteristics based on a recipe.
Figure 16E:
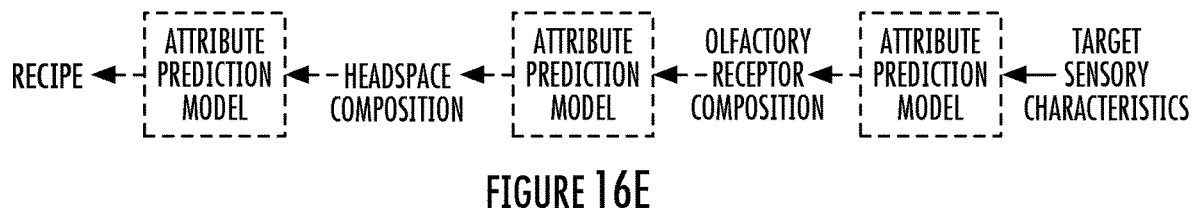
FIG. 16E depicts an example of predicting sample attributes based on target sensory characteristics.

In a third variant, the sample attributes can be predicted using an attribute prediction model (e.g., composition prediction model). Inputs to the attribute prediction model can include a first set of attributes, target sensory characteristics, and/or any other inputs. Outputs from the attribute prediction model can include a second set of attributes and/or any other outputs. In examples, the attribute prediction model can be a trained composition model, wherein a sample composition can be predicted using the trained composition model. In a first example, the attribute prediction model can predict an olfactory receptor composition and/or a gustation composition for a sample based on a (measured) headspace composition for the sample and/or sample attributes; example shown in FIG. 16A. This model can be trained using a set of headspace compositions associated with olfactory receptor composition and/or gustation compositions measured for each of a set of training samples, or be otherwise trained. In a second example, the attribute prediction model can predict an olfactory receptor composition and/or gustation composition for a sample based on process parameters, ingredients, a sample recipe, sample context, molecular structure, and/or any other attributes (e.g., predetermined attributes, retrieved sample attributes, measured attributes, etc.); example shown in FIG. 16C This model can be trained using a set of sample attributes associated with olfactory receptor composition and/or gustation compositions measured for each of a set of training samples, or be otherwise trained. In a specific example, the attribute prediction model can function to predict which components are likely to be overrepresented in the olfactory receptor composition and/or the gustation composition relative to the headspace composition. In a third example, the attribute prediction model can predict a sample or headspace composition based on the process parameters, ingredients, a recipe, sample context, and/or other attributes; examples shown in FIG. 16A and FIG. 16B. In a fourth example, the attribute prediction model can predict a sample context based on the process parameters, ingredients, recipe, and/or other attributes. In a fifth example, the attribute prediction model can predict an olfactory receptor composition, a headspace composition, a sample composition, ingredients, sample context, and/or process parameters based on: target sensory characteristics, a target olfactory receptor composition, a target headspace composition, a target sample composition, and/or any other suitable target; example shown in FIG. 16E. In a sixth example, a combination of examples can be used. In a specific example, the attribute prediction model can predict an olfactory receptor composition and/or gustation composition for a sample based on at least one of: headspace composition, (manufacturing) process parameters, (manufacturing) ingredients, a sample recipe, sample context, molecular structure (e.g., of one or more sample components), and/or any other attributes. However, the attribute prediction model can predict any other suitable set of attributes.

The attribute prediction model can include or use classical machine learning models (e.g., regularization, linear regression, logistic regression, decision tree, SVM, nearest neighbor, PCA, SVC, LDA, LSA, t-SNE, naïve bayes, k-means clustering, clustering, association rules, dimensionality reduction, kernel methods, genetic programs, support vectors, etc.), neural networks (e.g., CNN, CAN, LSTM, RNN, autoencoders, deep learning models, etc.), ensemble methods, rules, heuristics, deterministics, classification, equations (e.g., weighted equations, etc.), selection (e.g., from a library), optimization methods (e.g., Bayesian optimization. multi-objective Bayesian optimization, Bayesian optimal experimental design, etc.), Markov methods (e.g., hidden Markov models), statistical methods, probability methods, comparison methods (e.g., matching, distance metrics, thresholds, etc.), and/or any other suitable method or model. The attribute prediction model can be or include scoring models, numerical value predictors (e.g., regressions), classifiers (e.g., binary classifiers, multiclass classifiers, etc.), and/or provide other outputs.

The attribute prediction model can be trained, learned, fit, predetermined, and/or can be otherwise determined. The attribute prediction model can be learned using: self-supervised learning, semi-supervised learning, supervised learning, unsupervised learning, reinforcement learning, transfer learning, Bayesian optimization, positive-unlabeled learning, using backpropagation methods, and/or otherwise learned. The attribute prediction model can be learned or trained on: labeled data (e.g., data labeled with the target label), unlabeled data, positive training sets (e.g., a set of data with true positive labels, negative training sets (e.g., a set of data with true negative labels), and/or any other suitable set of data. For example, training the attribute prediction model can include determining (e.g., measuring) a first and second set of attributes, and training the attribute prediction model to predict the second set of attributes based on the first set of attributes. However, the attribute prediction model can be otherwise trained.

In a fourth variant, a combination of the first, second, and/or third variants can be used (e.g., determining a first set of attributes using the first variant, a second set of attributes using the second variant, and a third set of attributes using the third variant).

One or more sample attributes can optionally be parameterized (e.g., wherein the parameterized attributes can be used in all or parts of the method as the sample attributes). In variants, the parameterized attributes can be used to normalize sensory data (e.g., for a sensory panelist, for a matrix, etc.), be used in place of sample attributes, be used as an input to one or more models, be used to adjust one or more models (e.g., shifting a sensory function), and/or otherwise used. In a first example, matrix attributes can be parameterized into a vector of values corresponding to matrix properties. Examples of matrix properties include: matrix composition (e.g., percent fat, percent water, etc.), matrix density, matrix porosity, matrix fibrosity, matrix size, matrix structure, matrix functional properties, and/or any other matrix properties. In a second example, matrix attributes can be parameterized into a value representing a matrix identifier (e.g., a semantic label, an identifier mapping to a substrate with a specified composition and/or process parameters, etc.). In a third example, sensory panelist attributes can be parameterized into a vector of values representing how the sensory panelist shifts a sensory function. In a fourth example, sensory panelist attributes can be parameterized into a vector of values representing the sensory panelist demographics and/or any other sensory panelist information, etc.). In fifth example, sensory panelist attributes can be parameterized into a value representing a sensory panelist identifier.

However, sample attributes can be otherwise determined.

Collecting sensory data for the sample S200 functions to generate a dataset of sample comparisons based on perceived sensory characteristics (e.g., perceived sensory intensity). S200 can be performed after S100, after S600 (e.g., to validate a predicted sensory characterization and/or sensory similarity), and/or at any other time.

Sensory characteristics can include: flavor characteristics, taste characteristics (e.g., pre-mastication taste, aftertaste, finish, etc.), texture characteristics (e.g., texture profile, firmness, toughness, puncture, stretch, compression response, mouthfeel, viscosity, graininess, relaxation, stickiness, chalkiness, flouriness, astringency, crumbliness, stickiness, stretchiness, tearability, mouth melt, etc.), appearance characteristics (e.g., color, sheen, etc.), odor characteristics (e.g., aroma, retronasal aroma, orthonasal aroma, etc.), and/or characteristics for other sensory modalities. Sensory characteristics are preferably perceived characteristics, but can additionally or alternatively be measured and/or inherent characteristics. The sensory characteristics can include: a quality (e.g., odor quality, such as "apple" or "buttery,"; taste quality, such as "salty" or "sweet"; etc.), an intensity, hedonic tone, and/or any other characteristic.

S200 can be performed for a set of samples (e.g., all combinations of the set of samples, a subset of combinations of the set, a set of prototype and/or target samples, etc.). For example, the set of samples can be a set of training samples. In a first variant, the set of samples includes samples of the same component (e.g., molecule) at different concentrations for one or more components. In an example, each sample includes substantially a single component at a given concentration. In a second variant, the set of samples includes one or more samples of different mixtures of the same components at different concentrations. In an example, each sample includes two or more components, wherein each sample varies in the relative proportion of the components. In a third variant, the set of samples includes one or more samples of different mixtures of different components at different concentrations. However, the sample set can be otherwise constructed. The set of samples (e.g., two or more samples, a single sample, etc.) and/or one or more sample combinations can be selected from a larger set. This selection can function to determine the next samples to compare (e.g., the optimal samples to train the sensory characterization model using minimal data, the optimal samples to reduce model uncertainty, etc.). The selection can be performed randomly, using bracket-based selection, using uncertainty quantification (e.g., via the Bradley-Terry-Luce model), using active learning selection, using Bayesian optimization methods, and/or via any other selection method. In a specific example, subsets from the set of samples can be selected, wherein one or more sensory panelists compare samples within a subset. The subsets are preferably selected such that the subsets contain overlapping samples and/or overlapping sensory panelists (e.g., multiple sensory panelists assigned to rank and/or rate Sample A), but can be otherwise selected.

The sensory data is preferably subjective (e.g., a sensory panelist comparing perceived sensory intensity between samples), but can alternatively be objective (e.g., sensory data determined directly based on the sample attributes). The sensory data is preferably relative—a comparison between two or more samples (e.g., a ranking)—but can alternatively be absolute (e.g., a score), a classification, a description (e.g., a flavor descriptor selection, an audio or text description, etc.), or be any other suitable characterization of the sample. The sensory data can be collected for a given sensory quality (e.g., for each sensory quality in a set of qualities) and/or for a sample overall. For example, the sensory data can include a value for each of a set of taste modalities (e.g., salty, savory, sour, sweet, or bitter, etc.), each of a set of flavor descriptors or odor qualities (e.g., floral, grassiness, etc.), an overall value (e.g., pungent, weak, etc.), and/or values for other sensory attributes. The sensory data is preferably collected using comparisons performed by sensory panelists (e.g., human subjects), but can be collected using olfactometers, assays and/or assay tools, and/or other methods. The sensory panelists preferably span a range of demographics (e.g., age, sex, etc.), but can alternatively be otherwise selected.

The sensory data (e.g., flavor data) can include odor data (e.g., related to orthonasal olfaction and/or retronasal olfaction), taste data (e.g., related to tongue taste, gustation, etc.), chemesthetic data, texture data, appearance data, any combination thereof, and/or any other data associated with sensory characteristics. The sensory data can be acquired as ratings, rankings, scores, labels, and/or other measures; assessed as intensities, qualities, similarities, and/or other assessments; can be acquired via other evaluation approaches; and/or acquired using any combination thereof.

Rankings can be a relative position of the sample relative to one or more other samples, and ratings can be specific to the sample (e.g., specific to the rating pool in which it was calculated; be an absolute measure of the sample's sensory qualities; etc.) and be used to determine rankings; however, ratings and rankings can be otherwise defined. Sensory similarity can be a perceived sensory similarity (e.g., overall, for a given sensory quality, etc.), a measured similarity (e.g., using quantitative techniques), and/or other similarity between two or more samples. Sensory data can include data assessing one or more sensory qualities (e.g., flavor qualities), sensory intensities (e.g., flavor intensities), and/or any other sensory characteristic. Sensory quality can include odor quality (e.g., fragrant, woody, minty, sweet, chemical, popcorn, lemon, fruity, pungent, decayed, etc.), taste quality (e.g., sweet, salty, sour, bitter, umami, etc.), texture quality (e.g., firmness, toughness, stretchiness, graininess, stickiness, chalkiness, flouriness, astringency, crumbliness, stickiness, stretchiness, tearability, mouthfeel, meltability, etc.), appearance quality (e.g., shininess, matte, etc.), and/or any other quality. The sensory quality can additionally or alternatively be defined by the sensory characteristic of another sample (e.g., as a reference); this sensory quality definition can optionally be used when evaluating sensory similarity between two samples (e.g., two test samples, a prototype sample and a reference sample). The sensory quality can be a label (e.g., "lemony", "salty", etc.), a relationship (e.g., "more lemony", "saltier", etc.), a score (e.g., 5/10 lemoniness), and/or otherwise evaluated. Sensory intensity can be a strength (e.g., perceived strength) of a sensory characteristic. The sensory intensity can be determined for a given sensory quality (e.g., strength of the "lemon" odor) and/or for the overall sample. For example, a sensory intensity can be determined for each of a set of sensory qualities. The sensory intensity is preferably collected as a relationship between two or more samples (e.g., sample A is more intense (>) than sample B, sample A is much more intense (>>) than sample B, sample A is N times more intense than sample B, sample A is as intense as (~) sample B, etc.), but can additionally or alternatively be collected as an absolute score (e.g., sample A has an intensity of "5" or "very strong") or have any other format.

In a first variant, collecting sensory data includes ranking perceived sensory intensity and/or similarity (e.g., for a given sensory quality, for the sample overall, etc.) between two or more samples. The ranking can be pairwise (e.g., Sample 1>Sample 2), a single sample compared to multiple other samples (e.g., Sample 1>Sample 2 and Sample 1<Sample 3), multiple samples ranked together (e.g., Sample 1>Sample 3>Sample 2), use simple equality or inequality judgements, use categorical judgments (e.g. "higher," "more", or ">"; "much higher," "much more," or ">>"; "similar" or "~", etc.), and/or any other ranking system. For example, a sensory panelist ranking (e.g., flavor ranking, sensory ranking, etc.) can include an intensity ranking for each of a set of flavor qualities for each of a set of training samples. In specific examples, the intensity ranking for a training sample can be: higher than another sample, lower than another sample, or similar to another sample. In a first illustrative example, a sensory panelist (e.g., human subject) is asked to smell and rank three samples according to perceived overall sensory intensity (e.g., odor intensity). In a second illustrative example, a sensory panelist is asked to perform two pairwise comparisons (e.g., Sample 1 versus Sample 2 and Sample 1 versus Sample 3) of the perceived sensory intensity for the sensory quality of "lemon." In a third illustrative example, a sensory panelist is asked to rank three samples in order of similarity to a target sample (e.g., Sample 1 is the most similar, Sample 3 is the least similar).

In a second variant, collecting sensory data includes rating the perceived sensory intensity and/or similarity of one or more samples (e.g., a discrete rating, a rating from a continuous scale, etc.). Examples of the rating can include rating on a quantitative scale (e.g., rating a sample sensory intensity on a scale of 1-6, rating a similarity between two samples on a scale of 1-10, etc.), rating on a scale with references and/or anchors (e.g., a gLMS scale with logarithmically spaced verbal references, a scale with physical samples that users can smell as references, etc.), rating using a visual analog scale, a binary rating (e.g., whether two samples are similar or different), rating relative to the population of samples, and/or any other rating system. The rating can be determined by the human subject (e.g., rater), be calculated from rankings (e.g., determined using the first variant), and/or otherwise determined.

In a third variant, collecting sensory data includes collecting both ranking and rating data. In a first example, the samples are ranked with additional quantitative contextual information (e.g., Sample 1 has a sensory intensity that is approximately twice Sample 2; a sensory panelist positions a set of samples on a numbered chart and/or scale relative to one another; etc.). In a second example, the samples are ranked with additional qualitative contextual information (e.g., Sample 1 has a much higher intensity than Sample 2, Sample 1 has a slightly higher intensity than Sample 3, etc.).

Collected sensory data can optionally be associated with a sensory panelist (e.g., human subject), environmental parameters, and/or any other information (e.g., wherein the sensory data and associated information is stored in a database). For example, sensory data can be associated with the sensory panelist who ranked and/or rated the set of samples, and/or the environmental parameters (e.g., time, temperature, humidity, sample testing sequence, etc.) the sensory panelist and/or the samples were exposed to during sensory data collection. This metadata can be used to normalize each sample's score (e.g., normalized for panelist preferences, etc.), used as a search key, and/or otherwise used.

However, the sensory data can be otherwise determined.

The method can optionally include transforming the sensory data into a score S250, which can function to convert the sensory data for model training and/or validation. S250 can be performed after S200 (e.g., after each comparison, after a comparison batch, etc.) and/or at any other suitable time. The score (e.g., a sensory score) can be for a single sample, for a comparison between two or more samples, for a sample component, and/or be otherwise defined relative to one or more samples. A score can optionally be a sensory characterization (e.g., wherein the score is of the same form as sensory characterizations described in S300).

Figure 14:
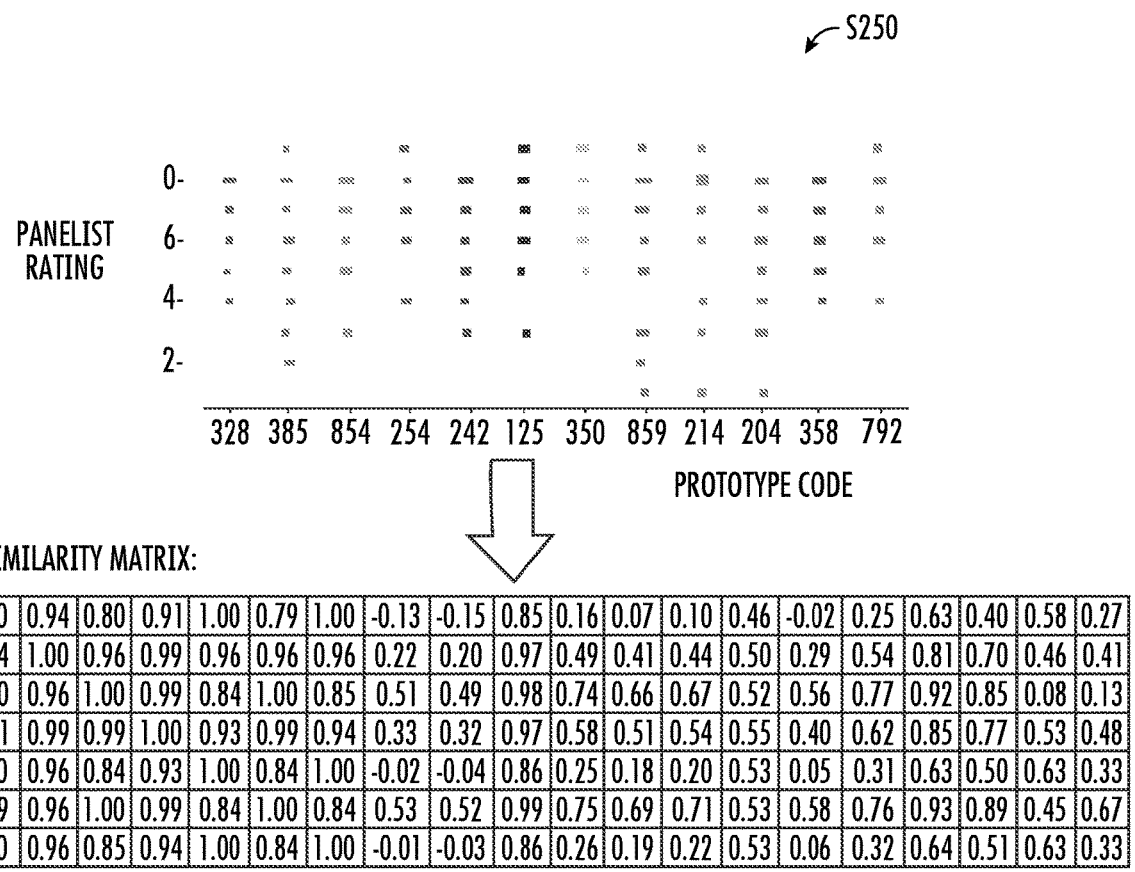
FIG. 14 depicts an illustrative example of determining scores based on sensory data.

In an example, the score can be a quantitative ranking and/or rating score for a sample. Specific score examples include an ELO score, a Glicko rating, a Plackett-Luce model output, a probability, and/or any other comparison-based metric. In a first specific example, a Plackett-Luce model framework is used to estimate a score for each sample in a set, where the inputs to the model include the sensory data for a set of samples (e.g., including sample rankings). In a second specific example, the rating and/or ranking collected from a sensory panelist is transformed to a score (e.g., using a predetermined mapping between ratings/rankings to scores, using a model, etc.). In a first illustrative example, for a given sensory panelist: a ranking of 'Sample A is much more intense (>>) than Sample B' is mapped to a probability of 100% that Sample A ranks above Sample B; a ranking of 'Sample A is more intense (>) than Sample B' is mapped to a probability of 75% that Sample A ranks above Sample B; and a ranking of 'Sample A is similar to (~) Sample B' is mapped to a probability of 50% that Sample A ranks above Sample B. In a second illustrative example, a similarity matrix can be determined based on the sensory data, wherein the similarity matrix includes a similarity score between each pair of samples (e.g., example shown in FIG. 14). In a third illustrative example, a sample rating can be calculated based on the sample's relative ranking (e.g., using rating algorithms, such as the ELO rating system, Glicko rating system, etc.).

Figure 3A:
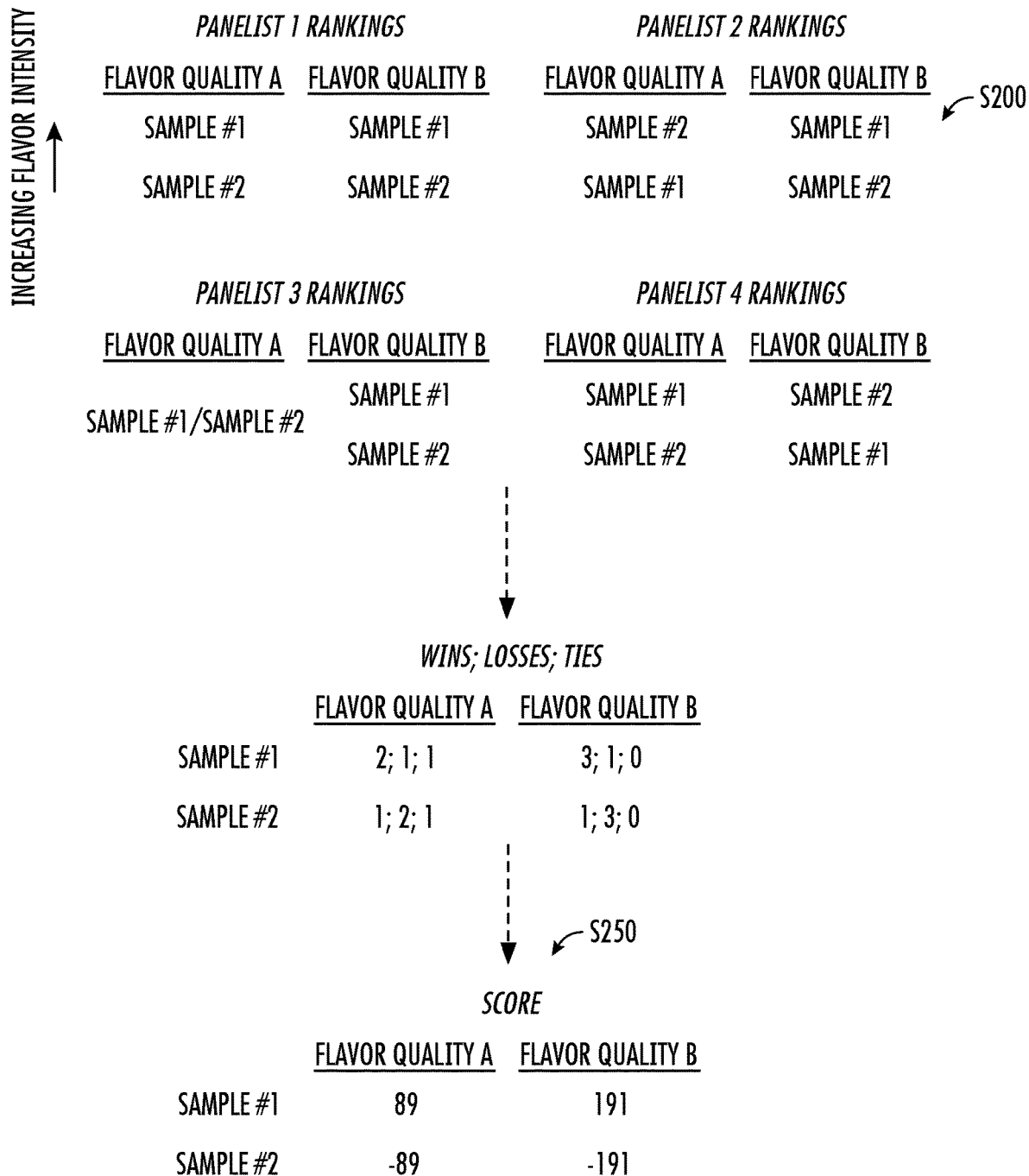
FIGS. 3A and 3B depict illustrative examples of transforming sensory data into a score.
Figure 3B:
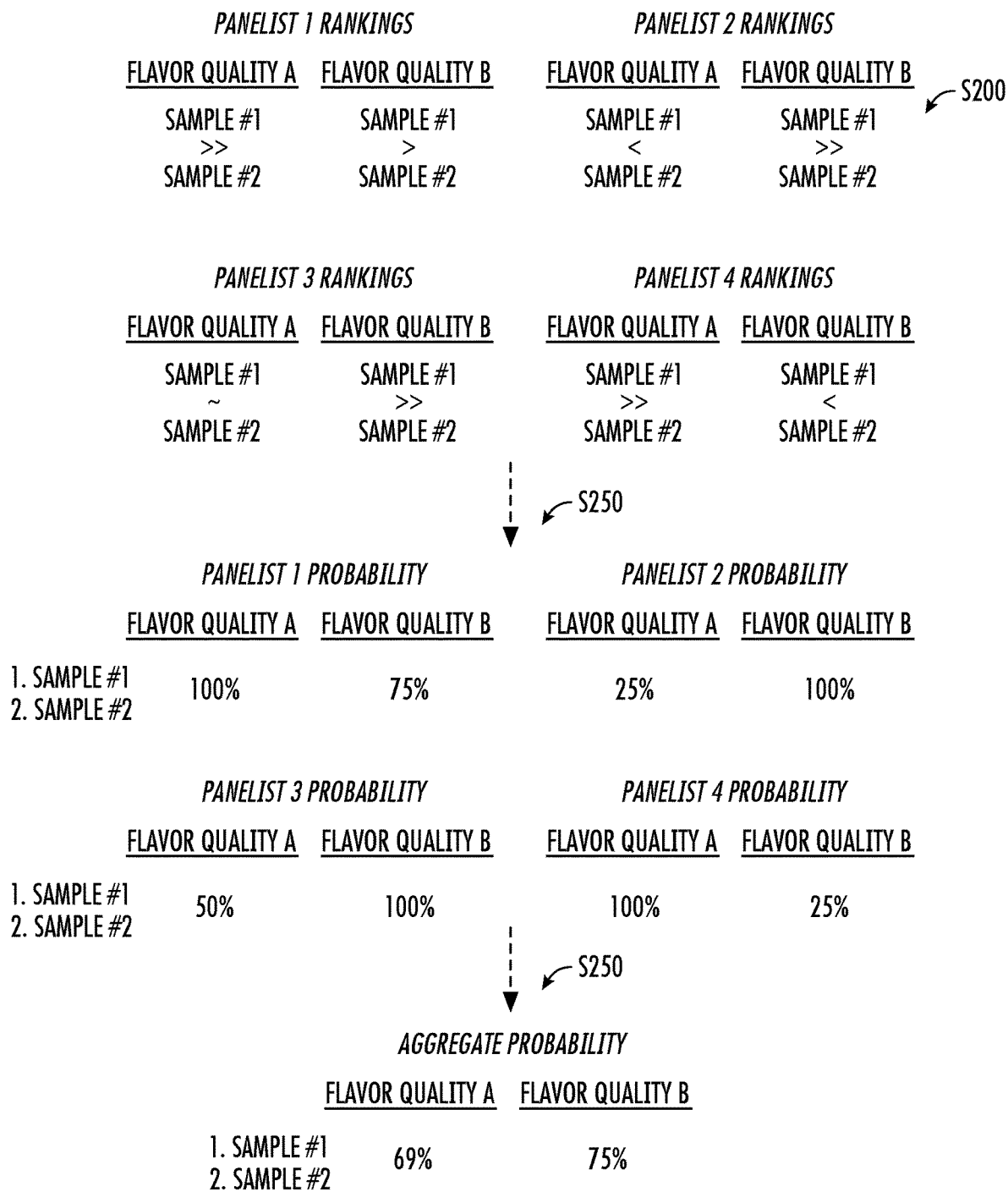

The score is preferably indicative of the sample's ranking amongst the sample set and/or provides quantitative information about how much better/worse the sample is one or more other samples; alternatively, the difference between two samples' scores can be indicative of the probability distribution for the samples' relative ranks, or be otherwise defined. Preferably, similar scores indicate similar perceived sensory characteristics (e.g., sensory intensity, sensory quality, both sensory intensity and sensory quality, etc.), as determined from the sensory data, but alternatively can indicate any other sensory information. In a first example, the score can be used to determine an overall ranking of a set of samples (e.g., wherein sensory data is collected for subsets of the set of samples). In a second example, the score can be used to compare samples that were not directly compared by one or more sensory panelists. In an illustrative example, two samples can be ranked relative to one another based on their respective scores, wherein each score is determined based on sensory data for the respective sample relative to other samples. In a third example, the score can be used to transform the sensory data such that it can be used to train the sensory characterization model. In a fourth example, the score can be used to aggregate sensory data across sensory panelists (e.g., examples shown in FIG. 3A and FIG. 3B). For example, each ranking and/or rating for an individual sensory panelist can be transformed into an intermediate score (e.g., 'Sample A>>Sample B' is transformed to a probability), wherein the intermediate scores can be aggregated (e.g., averaging, weighted averaging, median, any other statistical method, etc.) across sensory panelists to determine aggregated scores for the samples.

Sensory data and/or scores can optionally be normalized based on the sensory panelist and/or other metadata. For example, sensory data collected from sensory panelist 1 and/or scores derived from sensory data collected from sensory panelist 1 can be normalized based on the sensory data and/or scores for sensory panelist 1 relative to the sensory data and/or scores for one or more other sensory panelists (e.g., average rankings and/or rankings across sensory panelists for each sample comparison). However, sensory panelists and/or other metadata can be otherwise accounted for (e.g., using a mixed effect sensory characterization model).

Sensory data and/or scores can optionally be associated with uncertainty (e.g., an uncertainty parameter for each sample, for each score, for the overall sensory data and/or scores, etc.). In a first example, the uncertainty can be determined based on differences between panelist rankings and/or ratings. In a second example, the uncertainty can be determined by calculating scores using different subsets of the sensory data, and comparing the corresponding scores to determine the uncertainty.

However, the score can be otherwise determined.

Determining a sensory characterization model S300 functions to generate a model that can predict a sensory characterization given sample attributes and/or a model that can predict the similarity between two samples. S300 can be performed after S200, before S200, and/or at any other time.

The sensory characterization model (e.g., flavor model) can be a predictive model and/or any other model. The sensory characterization model can be a single model or an ensemble thereof (e.g., a component model and a mixture model). When the sensory characterization model includes multiple models, the models can be arranged in parallel, in series, and/or otherwise arranged. The sensory characterization model can include or use classical machine learning models (e.g., regularization, linear regression, logistic regression, decision tree, SVM, nearest neighbor, PCA, SVC, LDA, LSA, t-SNE, naïve bayes, k-means clustering, clustering, association rules, dimensionality reduction, kernel methods, genetic programs, support vectors, etc.), neural networks (e.g., CNN, CAN, LSTM, RNN, autoencoders, deep learning models, etc.), ensemble methods, rules, heuristics, deterministics, classification, equations (e.g., weighted equations, etc.), selection (e.g., from a library), optimization methods (e.g., Bayesian optimization. multi-objective Bayesian optimization, Bayesian optimal experimental design, etc.), statistical methods, probability methods, comparison methods (e.g., matching, distance metrics, thresholds, etc.), models leveraging or predicting sigmoid functions, and/or any other suitable method or model. The sensory characterization model can be or include scoring models, numerical value predictors (e.g., regressions), classifiers (e.g., binary classifiers, multiclass classifiers, etc.), and/or provide other outputs. The sensory characterization model can be trained, learned, fit, predetermined, and/or can be otherwise determined. For example, the sensory characterization model can be trained using S400 methods.

The sensory characterization model can be: specific to a sensory quality (e.g., grassiness model, floral model, etc.), specific to a component (e.g., methanethiol model, butanoic acid model, etc.), specific to a mixture, specific to a sample, specific to a context (e.g., specific to a sample matrix), specific to a sensory panelist, generic across sensory qualities (e.g., trained to output an overall sensory intensity, trained to output independent sensory intensity values for each of a set of sensory qualities, etc.), generic across components (e.g., trained to output a sensory intensity given the attributes of any molecule, trained to output a sensory intensity given a combination of components as the input, etc.), generic across mixtures, generic across samples, generic across contexts, generic across sensory panelists, trained to combine sensory intensities of constituent components and/or sensory qualities, and/or any combination thereof.

Figure 12:
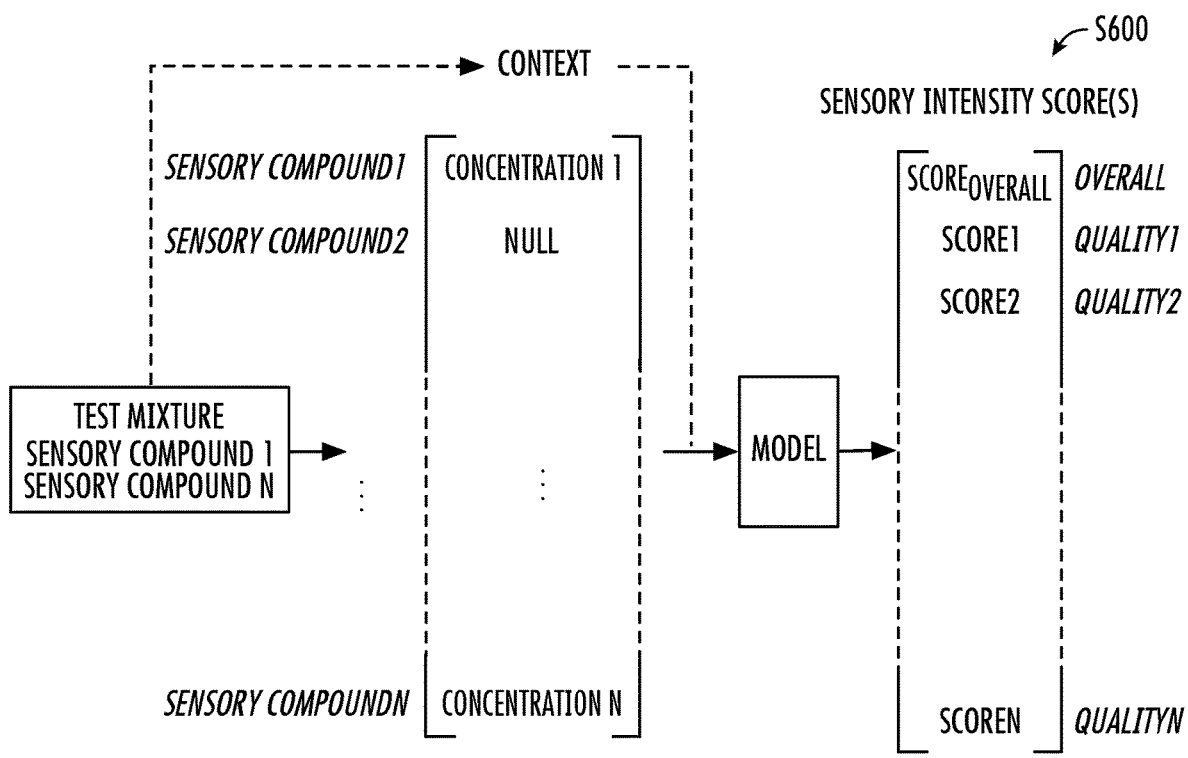
FIG. 12 depicts an illustrative example of an example model input vector and an example model output vector.

The sensory characterization model inputs can include sample attributes (e.g., examples shown in FIG. 16A, FIG. 16B, FIG. 16C, and FIG. 16D), sensory characterizations (e.g., output by a different sensory characterization model), and/or any other inputs. In examples, a model input vector can comprehensively represent all components under consideration (e.g., including a row for each component; example shown in FIG. 12), which can enable the resultant model to more accurately predict the sensory intensities for mixtures. In other examples, the model input vector can include values for a subset of all components under consideration (e.g., only components determined to be influential for a given sensory characteristic, etc.), include values for other sample attributes (e.g., context, molecular structure, etc.), and/or be otherwise configured. However, model inputs can be otherwise defined. The sensory characterization model outputs can include a sensory characterization, a sensory function (e.g., the sensory function itself, sensory function parameters, sensory function parameter adjustments, etc.), uncertainty parameters, and/or any other outputs.

Figure 8A:
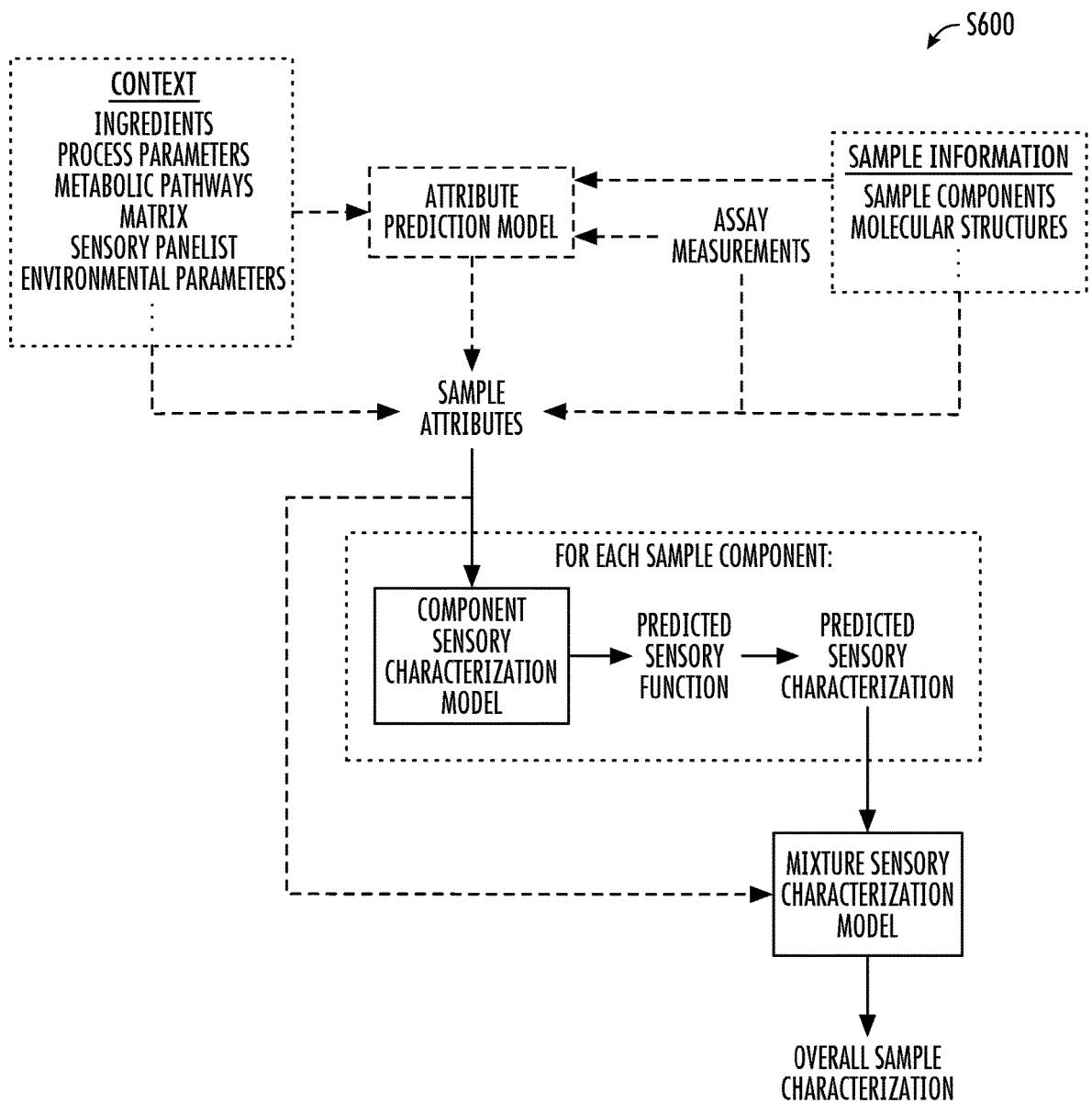
FIG. 8A depicts an example of predicting a sample characterization using a component model and a mixture model.

In a first variant, the model can be a neural network (e.g., CNN, DNN, etc.), trained to directly predict a sensory characterization given sample attribute values (e.g., for a mixture); example shown in FIG. 8A. In this variant, the model inputs can include the values for one or more sample attributes, and/or values for any other suitable set of inputs. In a first example, the model can be a multiclass classifier, and predict the probability that the sample will have each of a set of sensory characteristics (e.g., wherein each sensory characteristic is treated as a different class). In a second example, the model can predict a rating, ranking or other score for the sample. In a third example, the model can predict a sensory characterization curve or surface, such as a sensory function (e.g., a sigmoid curve) relating sensory intensity (e.g., for a sensory quality) and component amount (e.g., concentration), and/or predict the parameters describing the sensory characterization curve or surface.

Figure 8B:
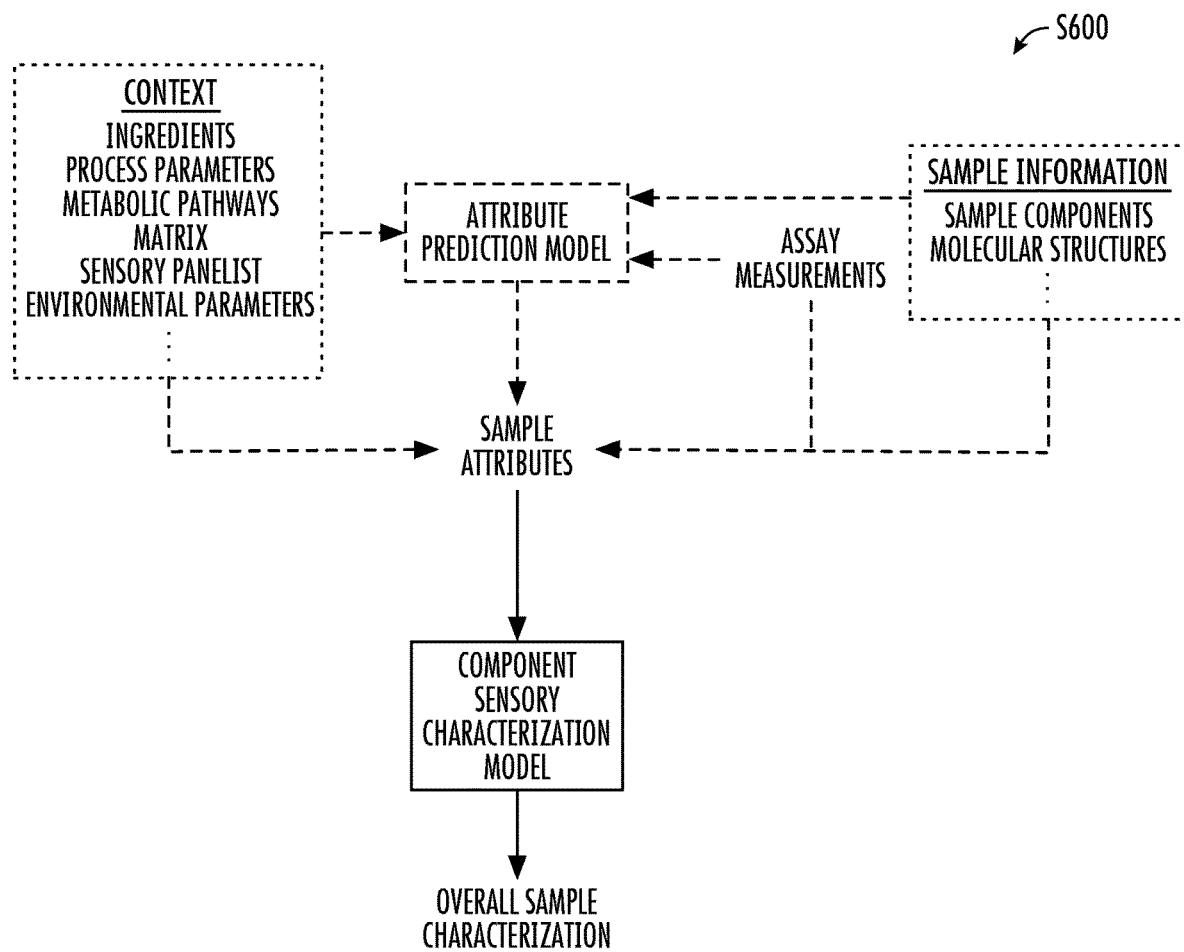
FIG. 8B depicts an example of predicting a sample characterization using a single sensory characterization model.

In a second variant, the sensory characterization model includes a first model (a component model) that can be used to determine sensory characterizations for individual components in the sample, and a second model (a mixture model) that can be outputs an overall sample sensory characterization based on the component sensory characterizations, sample attributes (e.g., context), and/or any other sensory characterization model inputs; example shown in FIG. 8B. For example, the component model can determine a component flavor characterization for each sample component (e.g., based on a component sensory function and the sample composition), and the mixture model can aggregate individual component sensory characterizations (e.g., including applying a transformation to the individual component sensory characterizations) to determine an overall sample sensory characterization (e.g., using a set of rules, heuristics, a regression, a neural network, etc.). The mixture model can aggregate the individual component sensory characterizations based on sample attributes (e.g., the transformation is based on the sample attributes) such as composition, context, and/or any other attributes.

In a first embodiment of the second variant, for each component in the sample, the component model outputs the component sensory characterizations based on sample attributes (e.g., a component identifier, a component amount, sample context, and/or any other sample attributes). In a specific example, the component model can include a mixed effects model, wherein the sample context (e.g., matrix attributes, sensory panelist attributes, etc.) is treated as a random effect and amount of the component in the sample is treated as a fixed effect. For example, the mixed effects model can enable the component model to account for differences between sensory panelists and/or other context differences.

Figure 13:
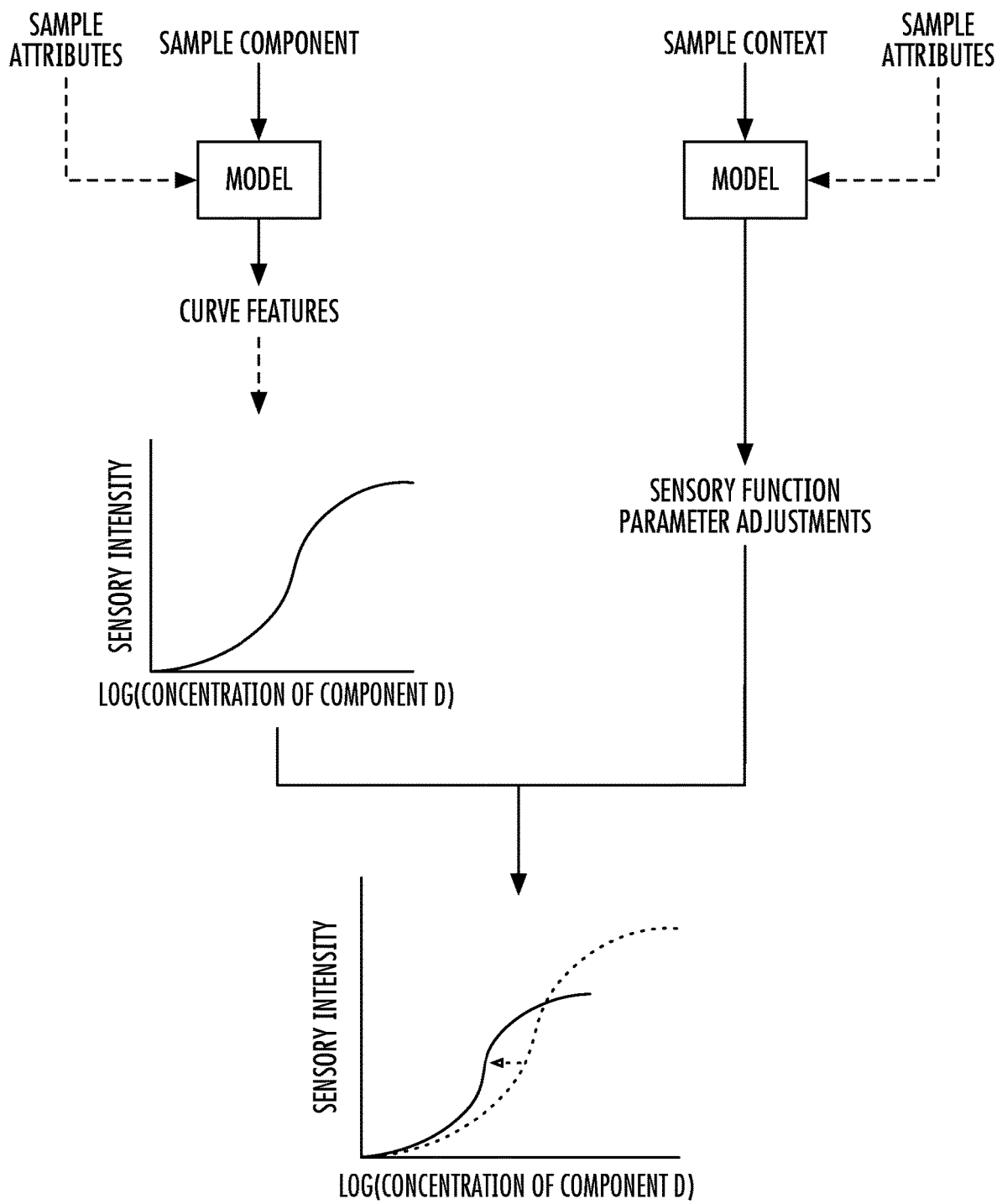
FIG. 13 depicts an example of determining sensory function parameter adjustments.

In a second embodiment of the second variant, for each component in the sample, the component model outputs a (component) sensory function based on sample attributes, wherein the sensory function can be used to determine the component sensory characterization. The sensory function (e.g., flavor function) preferably relates sample composition (e.g., component concentration) to a sensory characterization (e.g., a sensory intensity), but can additionally or alternatively relate other component and/or sample information. For example, a sensory characterization can be determined for a sample based on the sensory function and the composition for the sample. In an illustrative example, the sensory function can include a Hill equation model (e.g., a sigmoidal relationship between sensory intensity and log of component concentration) and/or any other sigmoid model (e.g., sigmoid function). The sensory function can be defined by a set of sensory function parameters. The sensory function parameters can include x offset (e.g., component concentration offset), y offset (e.g., sensory intensity offset and/or any other sensory characterization offset), any other offset, slope (e.g., at one or more points on the sensory function, an average slope, etc.), maximum value, and/or any other parameters defining the sensory function. In a first example, the component model can directly output a sensory function (e.g., sensory function parameters) based on sample attributes (e.g., based on a component identifier, sample context, and/or any other attributes). In a first specific example, the sensory function can be learned (e.g., a learned latent function) using sensory data (e.g., flavor training data) collected from a set of sensory panelists (e.g., S200). In a second specific example, the sensory function can be a function fit to sensory data (e.g., sensory data for single-component samples at one or more concentrations.). In a third specific example, the component model can retrieve a sensory function (e.g., from a database of sensory functions associated with component identifiers and/or sample attributes). In a second example, the component model can include a first model trained to output an initial sensory function (e.g., initial sensory function parameters) based on the component (e.g., a component identifier) and/or any other sample attributes, and a second model trained to output sensory function adjustments (e.g., sensory function parameter adjustments) based on the sample context and/or any other sample attributes. An example is shown in FIG. 13. In an illustrative example, matrix attributes, sensory panelist attributes, and/or any other context can result in the same adjustments to one or more sensory function parameters across different components.

The sensory characterization can define (e.g., quantitatively define) sensory characteristics of the sample (e.g., including sensory intensity and/or sensory quality information). The sensory characterization be: qualitative, quantitative, relative, relative, discrete, continuous, a classification, numeric, binary, a combination thereof, and/or be otherwise characterized.

In a first variant, the sensory characterization is a vector in feature space or sensory characterization vector space (e.g., including a length and direction). The vector length can be the sensory intensity and/or be correlated to sensory intensity, where the magnitude difference between two vectors can describe the difference in the sensory intensity of the respective samples. The vector direction can define and/or be correlated to sensory quality, where the angle distance between two vectors can describe the difference in the sensory qualities of the respective samples. For example, two samples can have different sample attributes but have little or no sensory quality and/or sensory intensity difference (e.g., when the two samples are sensory metamers). Alternatively, a difference in sample attributes results in a difference in the respective sample sensory characterizations.

The sensory characterization vector space can be parametrized by a set of features (e.g., physicochemical features and/or transformations thereof) of the sample (e.g., of the sample components). The features can be semantic and/or non-semantic features. In a first example, the features are qualities, such that the vector is defined in quality space (e.g., wherein each axis is a sensory quality), wherein the projection of the vector onto a given quality axis can correspond to the sample's intensity for that quality. In a second example, the features can include sample attributes, such as: molecular weight of a component, component concentration, octanol/water partition coefficient, matrix features, features calculated by computational chemistry software, features generated from latent embeddings of other models, physicochemical features and/or transformations thereof, and/or any other sample features. However, the features can be otherwise defined. The features can be selected during model training (e.g., S400), selected prior to model training (e.g., predetermined), selected using a feature selection model, selected using explainability and/or interpretability methods, and/or be otherwise selected. In an example, the features can be selected to increase correlation between vector length and sensory intensity.

Figure 5:
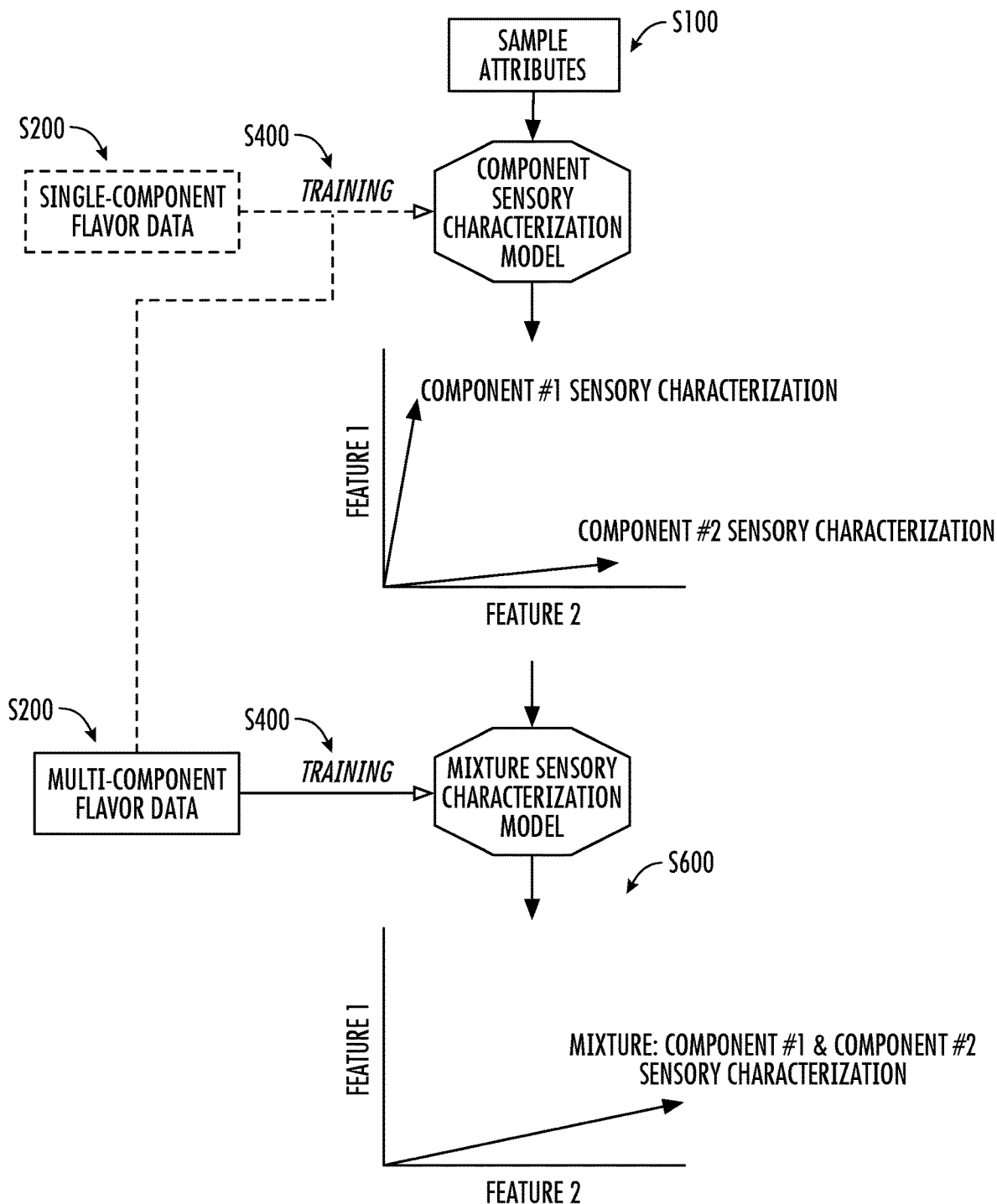
FIG. 5 depicts an example of determining a sensory characterization.

In an embodiment of the first variant, a first sensory characterization model (e.g., component model) can output one vector (e.g., in feature space) for each component (e.g., at a given concentration) in a mixture. The first sensory characterization model can be determined and/or trained using sensory data from S200 (e.g., with sensory data for single-component samples at one or more concentrations). The overall sensory characterization for the mixture can be determined using a second sensory characterization model (e.g., mixture model), where the component vectors act as inputs for the second model. The second model can include a transformation of the individual sample component vectors. An example is shown in FIG. 5.

Figure 6:
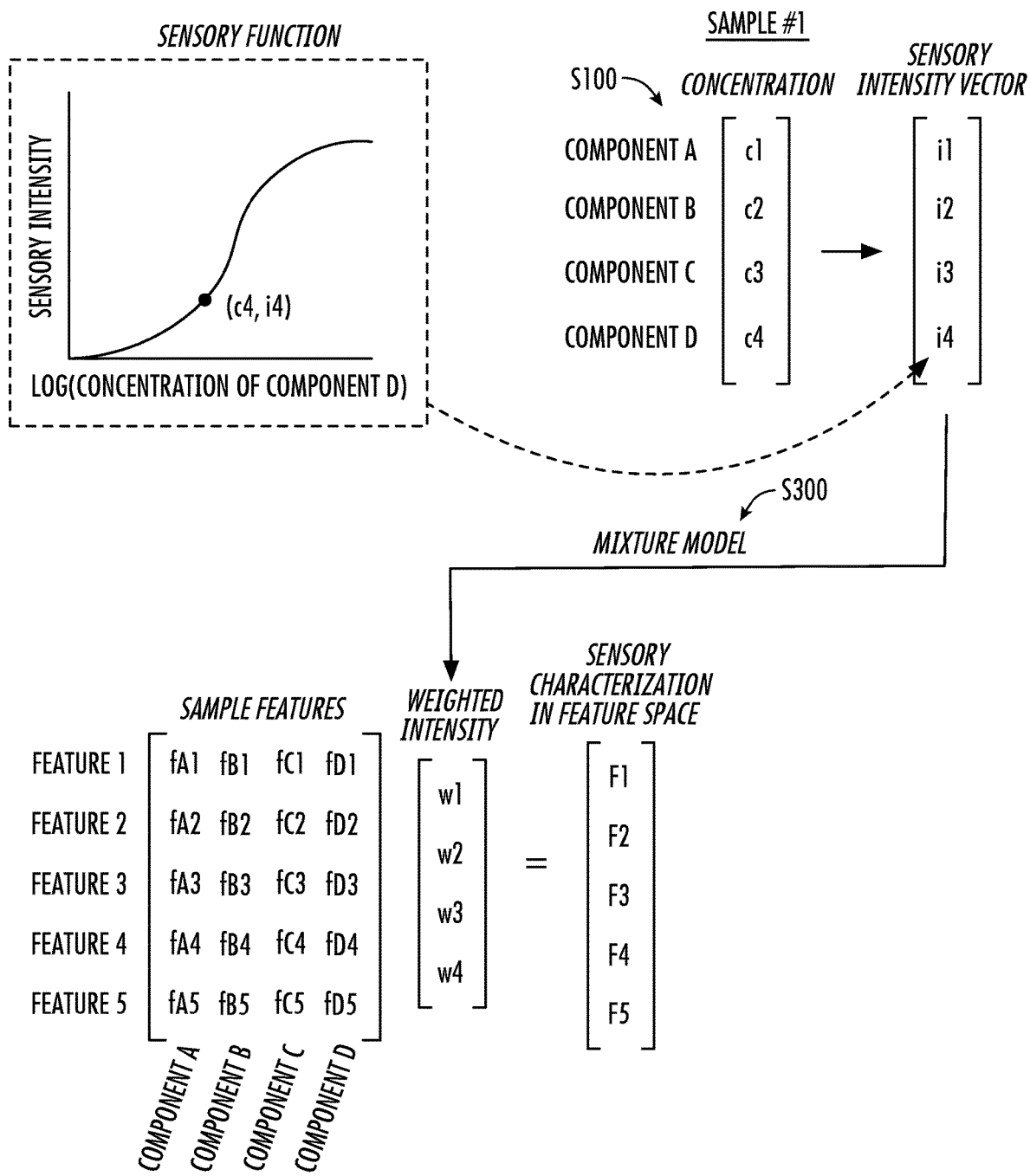
FIG. 6 depicts an illustrative example of determining a sensory characterization.

In a first example of the embodiment, the transformation includes a vector sum. In a second example of the embodiment, the transformation includes component interaction and/or weighting effects (e.g., accounting for one odorant overwhelming other odorants due to its high concentration relative to perceived sensory intensity). Weighting can be performed prior to vector summation and/or at any other time. A vector component weight can depend on a linear or nonlinear function of the component's sensory intensity (e.g., vector length, the angle between one vector and others, determined from S200, etc.). In a first illustrative example, only the most intense (e.g., high sensory intensity at the given concentration) one or more components of the sample contribute to the overall sample sensory characterization. In a second illustrative example, the weighting function can include $w_i = I_i^2$, where $w_i$ is the weight given to component i in a vector sum and $I_i$ is the sensory intensity of the component (e.g., which can be the component sensory characterization vector length). In a third example of the embodiment, a summation of the individual component vectors is projected into a lower dimensional subspace containing the features most represented by the most intense components in the sample. In a fourth example of the embodiment, the transformation includes a model trained in S400. An example is shown in FIG. 6.

In a second variant, the sensory characterization is a value and/or includes a value. In an example, the sensory characterization can be and/or include a score (e.g., of the same form as S200) for the sample. The score can be: correlated with the length of the sensory characterization vector (e.g., in feature space), correlated with the length of a projection of the sensory characterization vectors (e.g., onto a feature axis, onto another vector, etc.), determined based on a comparison between two sensory characterizations, and/or be otherwise defined.

In a third variant, the sensory characterization is a multi-dimensional surface representing sample(s) at multiple component amounts. In this example, the sensory characterization can include characterizations for multiple variants of a test sample mixture (e.g., with different mixing ratios, with different sample contexts, etc.).

In a fourth variant, the sensory characterization is a classification. In examples, the sensory characterization can be a sensory quality classification, a similarity classification (e.g., Sample A is: 'similar to Sample B', 'not similar to Sample B', 'greater intensity than Sample B', similar intensity to Sample B', 'less intensity than Sample B', etc.), and/or any other classification.

However, the sensory characterization model can be otherwise determined.

Training the sensory characterization model S400 can function to generate or update the sensory characterization model (e.g., the component model, the mixture model, etc.). S400 can be performed once, iteratively (e.g., for each new sample comparison, for each sample comparison batch, etc.), and/or at any other time. The model is preferably trained using the sample attributes (from S100) as training data and the sensory data and/or sensory scores (from S200 and/or S250) as training targets, but can be otherwise trained.

The sensory characterization model can be trained using: self-supervised learning, semi-supervised learning, supervised learning, unsupervised learning, reinforcement learning, transfer learning, Bayesian optimization, positive-unlabeled learning, using backpropagation methods, and/or otherwise learned. The sensory characterization model can be learned or trained on: labeled data (e.g., data labeled with the target label), unlabeled data, positive training sets (e.g., a set of data with true positive labels, negative training sets (e.g., a set of data with true negative labels), and/or any other suitable set of data.

Figure 2A:
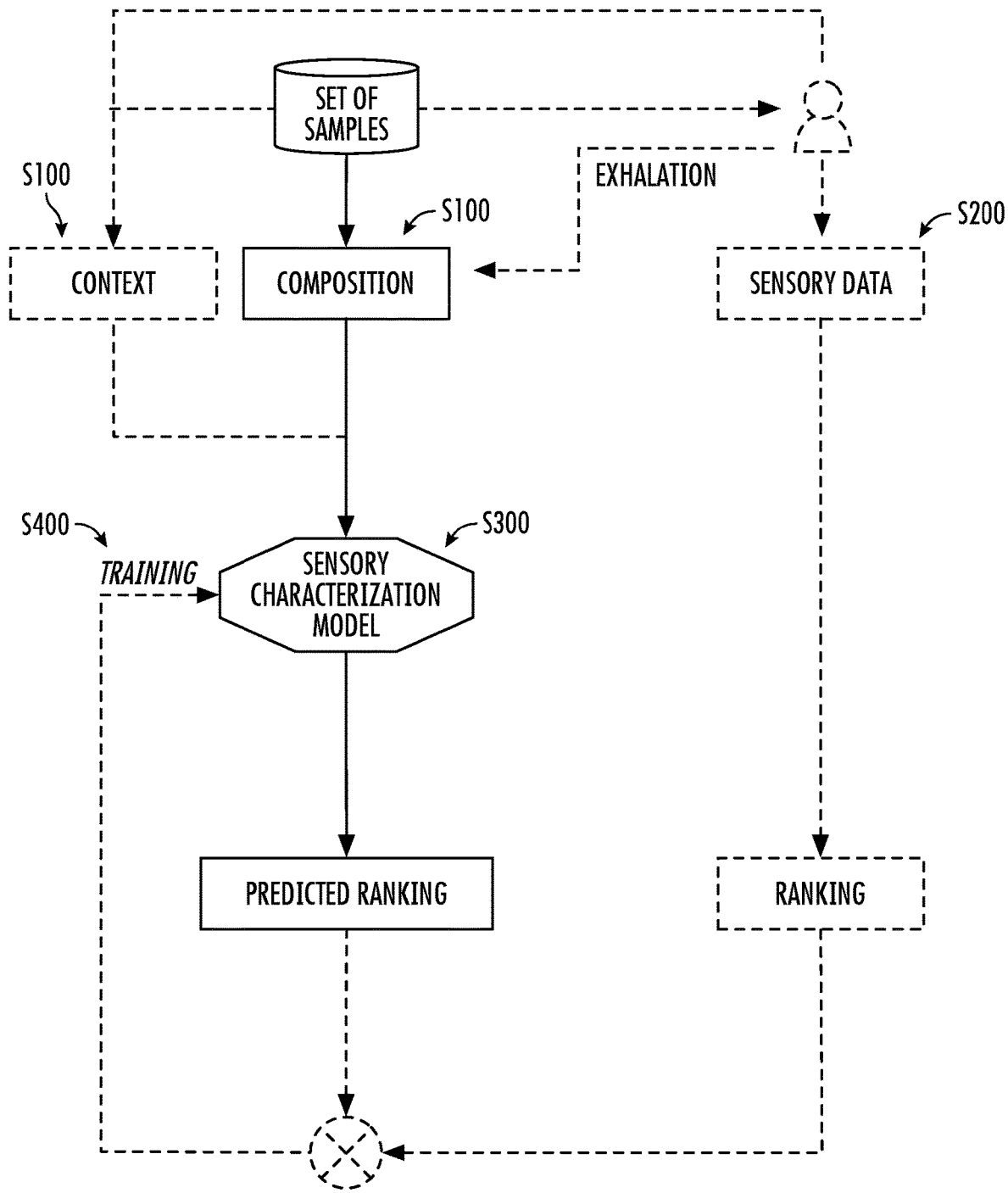
FIG. 2A depicts a first embodiment of the method, including training a sensory characterization model to predict a score.
Figure 2B:
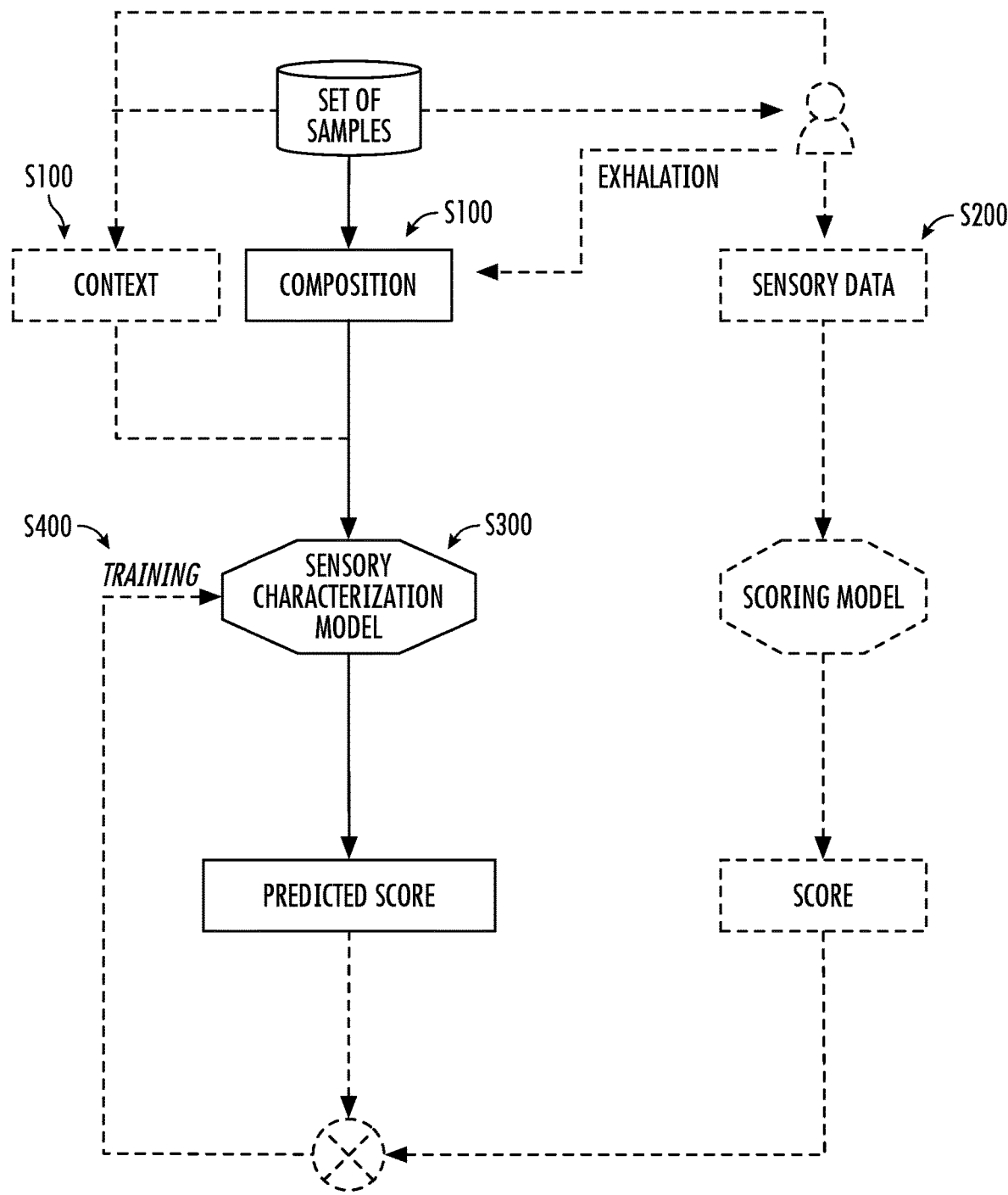
FIG. 2B depicts a second embodiment of the method, including training a sensory characterization model to predict a score.
Figure 7A:
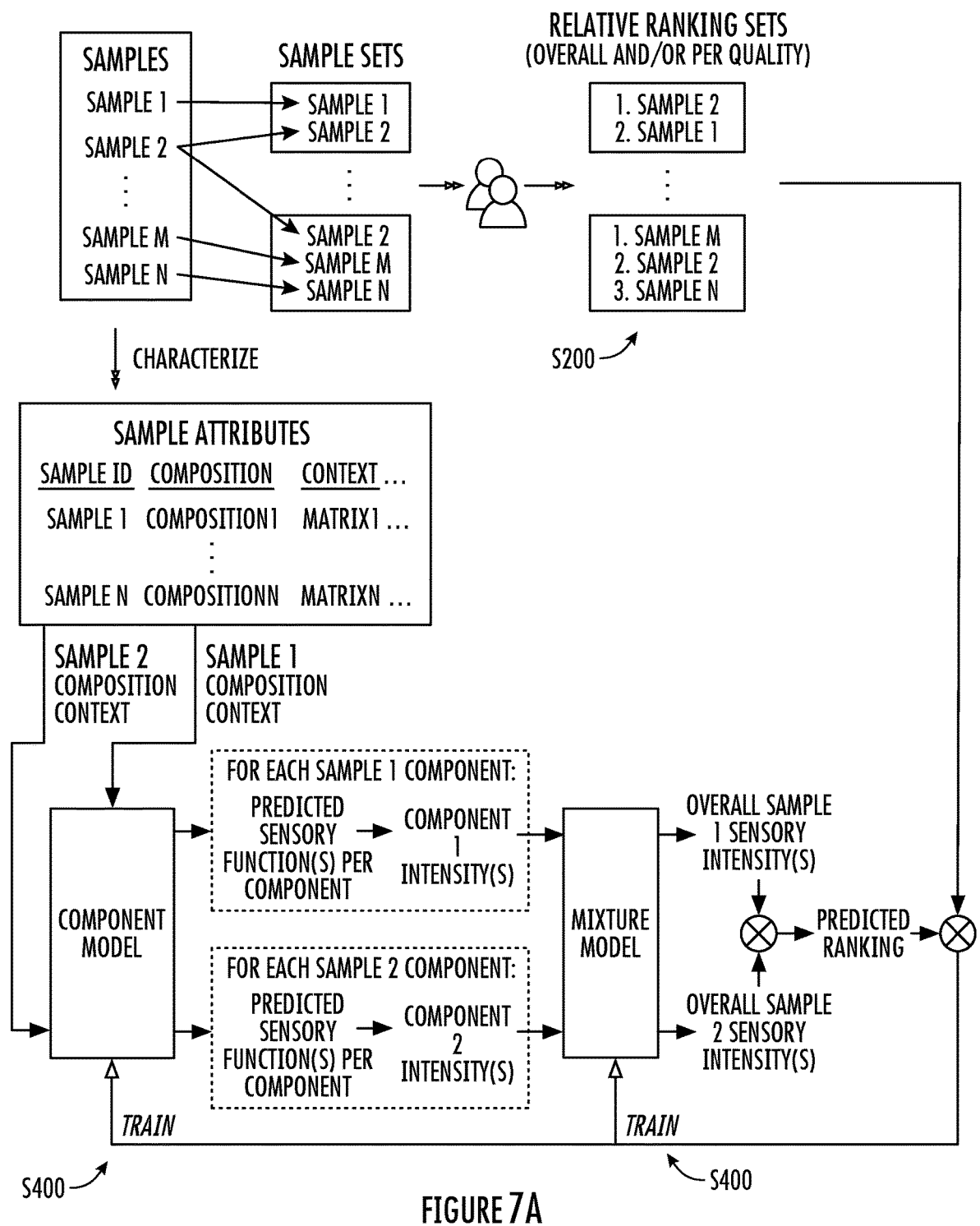
FIG. 7A depicts a first example of training a sensory characterization model, where the sensory characterization model includes a single model, including comparing a predicted ranking to an actual ranking.
Figure 7B:
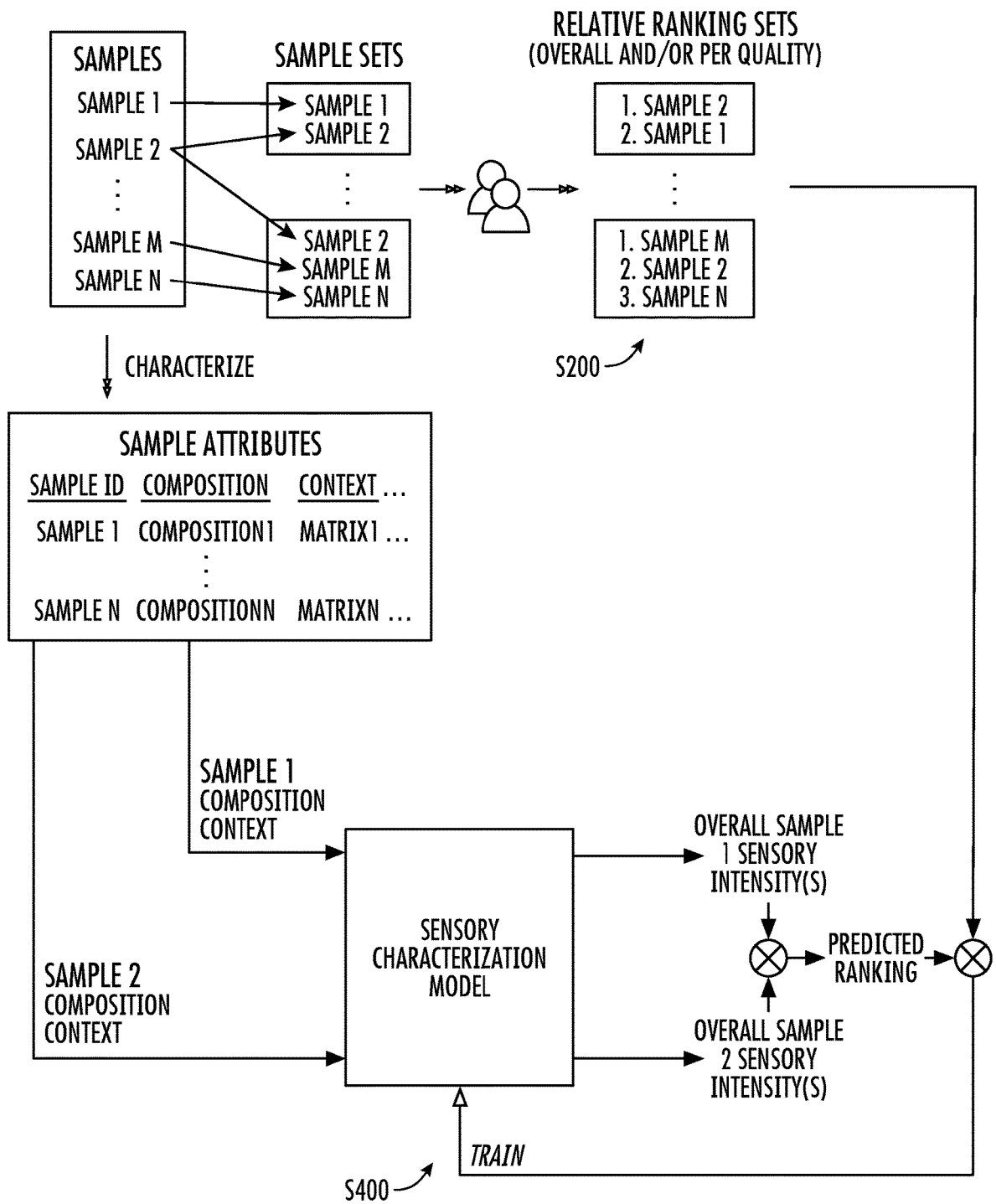
FIG. 7B depicts a second example of training a sensory characterization model, where the sensory characterization model includes a component model and a mixture model, including comparing a predicted ranking to an actual ranking.
Figure 7C:
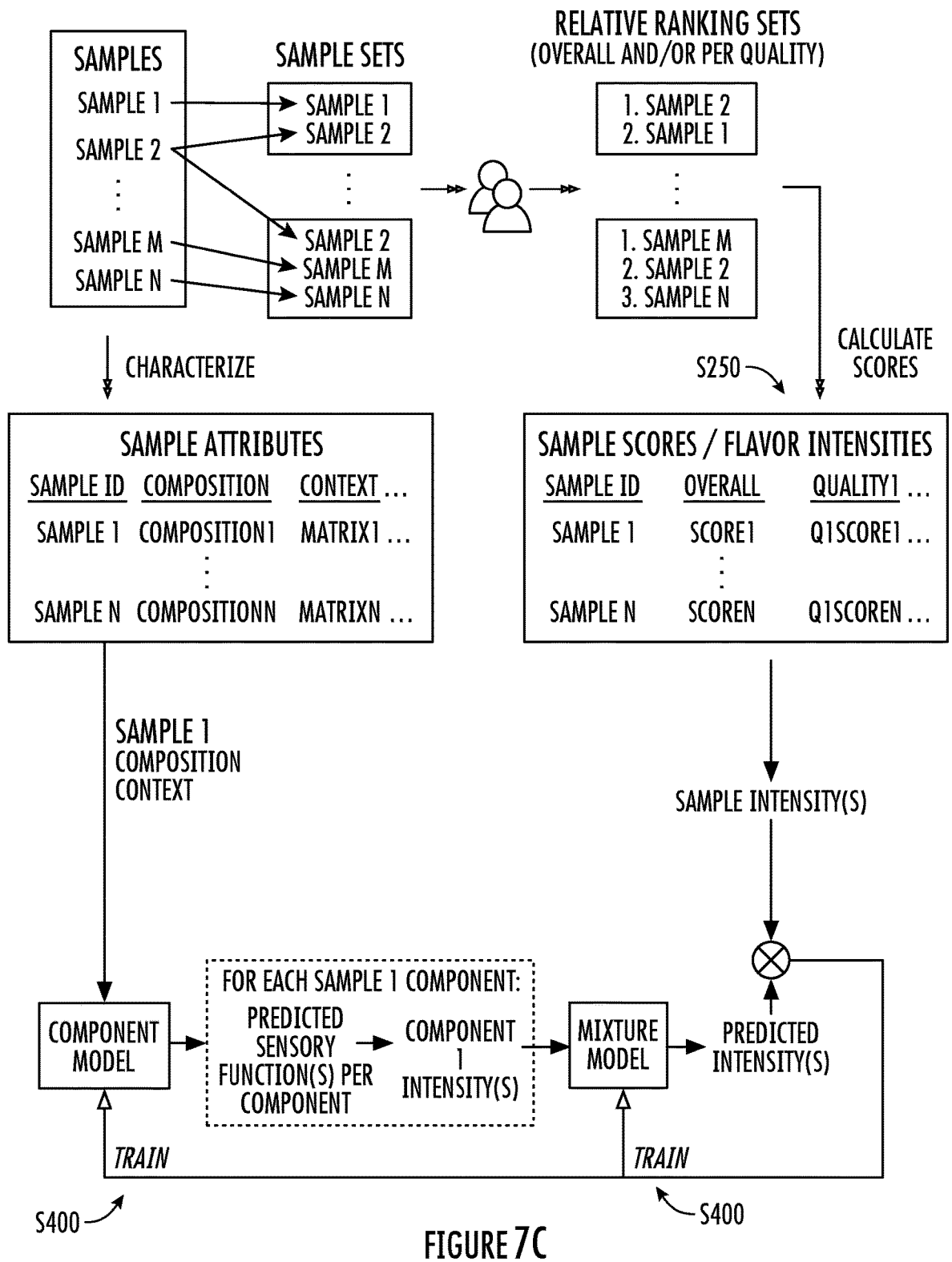
FIG. 7C depicts a third example of training a sensory characterization model, including comparing a predicted sensory characterization to a score.
Figure 7D:
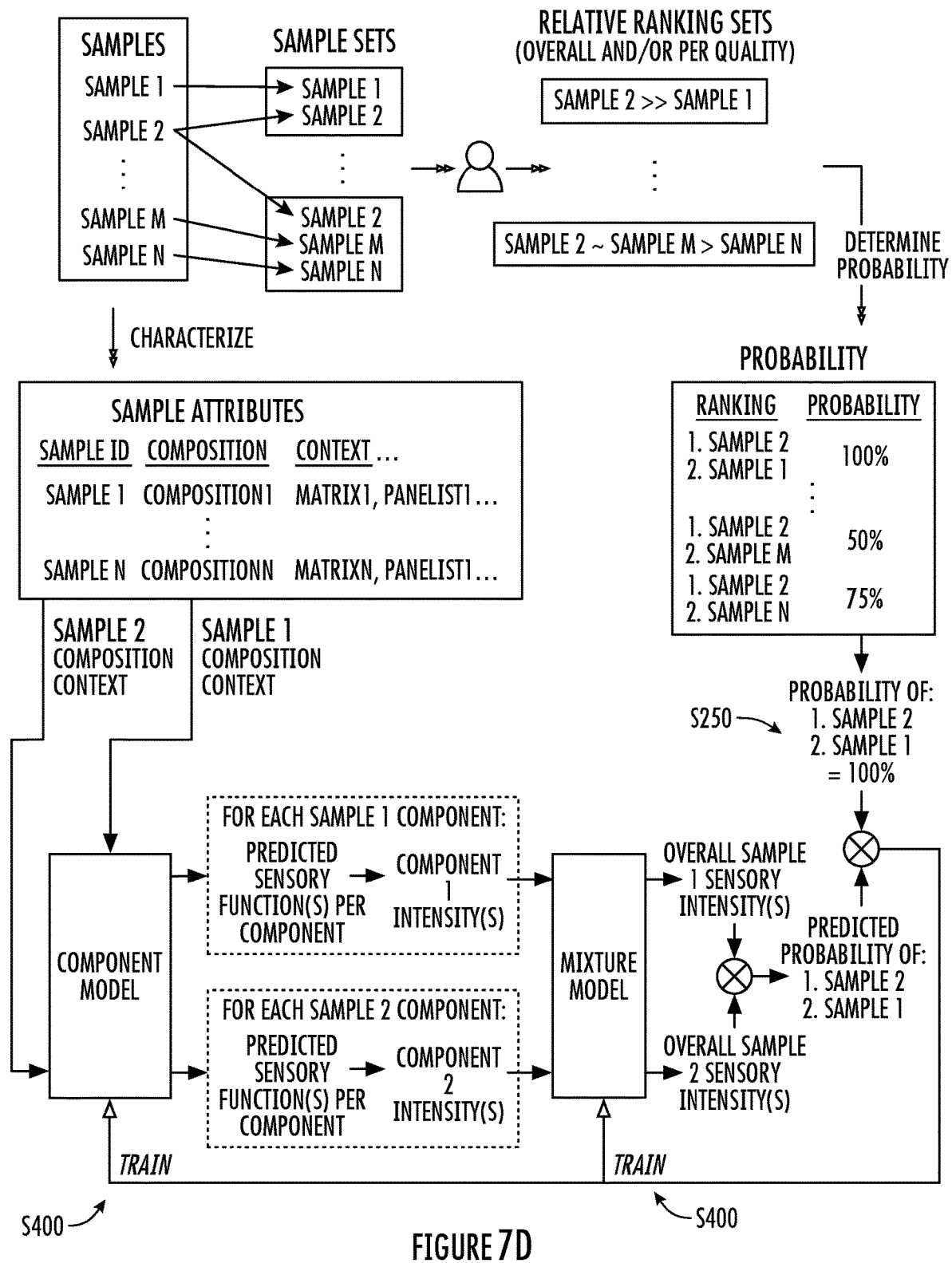
FIG. 7D depicts a fourth example of training a sensory characterization model, including comparing a predicted ranking probability for a sensory panelist to an actual ranking probability for the sensory panelist.
Figure 7E:
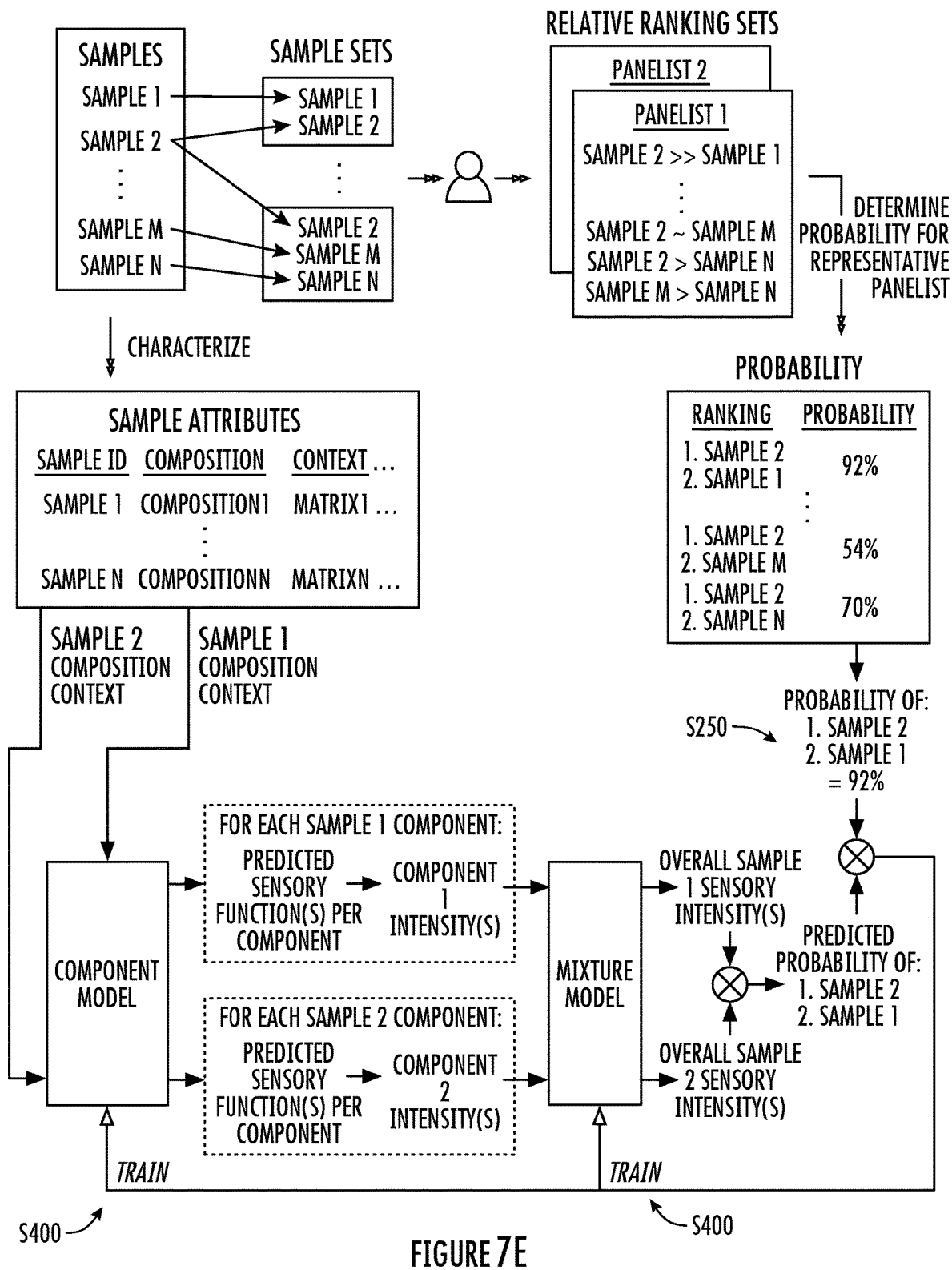
FIG. 7E depicts a fifth example of training a sensory characterization model, including comparing a predicted ranking probability to an aggregate ranking probability across sensory panelists.

In a first variant, S400 includes training the sensory characterization model as a single model. In a first embodiment, the sensory characterization model is trained to predict a sensory characterization (e.g., sensory intensity, sensory quality, rating, sensory score, etc.) for a sample given the sample attributes, wherein the sensory scores (from S250) are used as the training target. In a second embodiment, the sensory characterization model is trained to predict a sensory characterization (e.g., a sensory function) for two or more samples (e.g., the samples in S200's sample set, a subset of the samples in S200, etc.), wherein a predicted ranking (e.g., win/lose; ranking position; etc.) is determined based on the respective sensory characterizations, and the sensory characterization model is trained on the comparison between the predicted ranking and the actual ranking (from S200). In a specific example, the predicted ranking and/or the actual ranking can be a probability (e.g., a probability of a flavor ranking or other sensory ranking). In a third embodiment, the sensory characterization model predicts an overall ranking for one or more samples based on their predicted sensory characterizations (e.g., sensory scores), wherein the actual ranking (e.g., from S200) is used as the training target. In a fourth embodiment, the sensory characterization model is trained to predict the probability that impurities are present in a given sample (e.g., a single-component standard), the identity of the impurities, and/or the contribution of the impurities to the predicted sensory characterization (e.g., individually or in combination with the other compounds in the sample). In this embodiment, the sensory characterization model can optionally output an uncertainty parameter associated with the predicted sensory characterization for the given sample, wherein the uncertainty parameter can be based on sensory characterizations for the predicted impurities. Examples are shown in FIG. 2A, FIG. 2B, and FIG. 7B.

In a second variant, S400 includes training a component model and training a mixture model. The training data for the component model and the mixture model can be the same training data, overlapping training data, nonoverlapping training data, and/or otherwise related. The training data for the component model and/or the mixture model can include single-component samples and/or multi-component samples (e.g., mixtures).

In embodiments, S400 includes learning a sensory function (e.g., a latent sensory function, latent sensory function parameters, etc.). In an example, learning the sensory function can include learning the sensory function parameters (offset, slope, maximum value, etc.) and/or sensory function parameter adjustments. The sensory function can be learned using sensory data collected from a set of sensory panelists (e.g., S200). The sensory function can optionally be a component sensory function, wherein S400 can include learning a component sensory function for each sample component.

In a first example, S400 can include training the component model to learn the sensory function. In a specific example, the component model can be trained using the sensory data to determine (e.g., predict) the sensory function for a sample based on the sample composition, the sample context (e.g., parameterized context), and/or any other sample attributes. For example, training the component model can include using the component model to predict a sensory function for a sample, wherein the sensory function is used to predict sensory intensity based on component amount (e.g., concentration) and sample context (e.g., by querying the sensory function), wherein a known sensory intensity (e.g., from S250) can be used as a training target.

Figure 4:
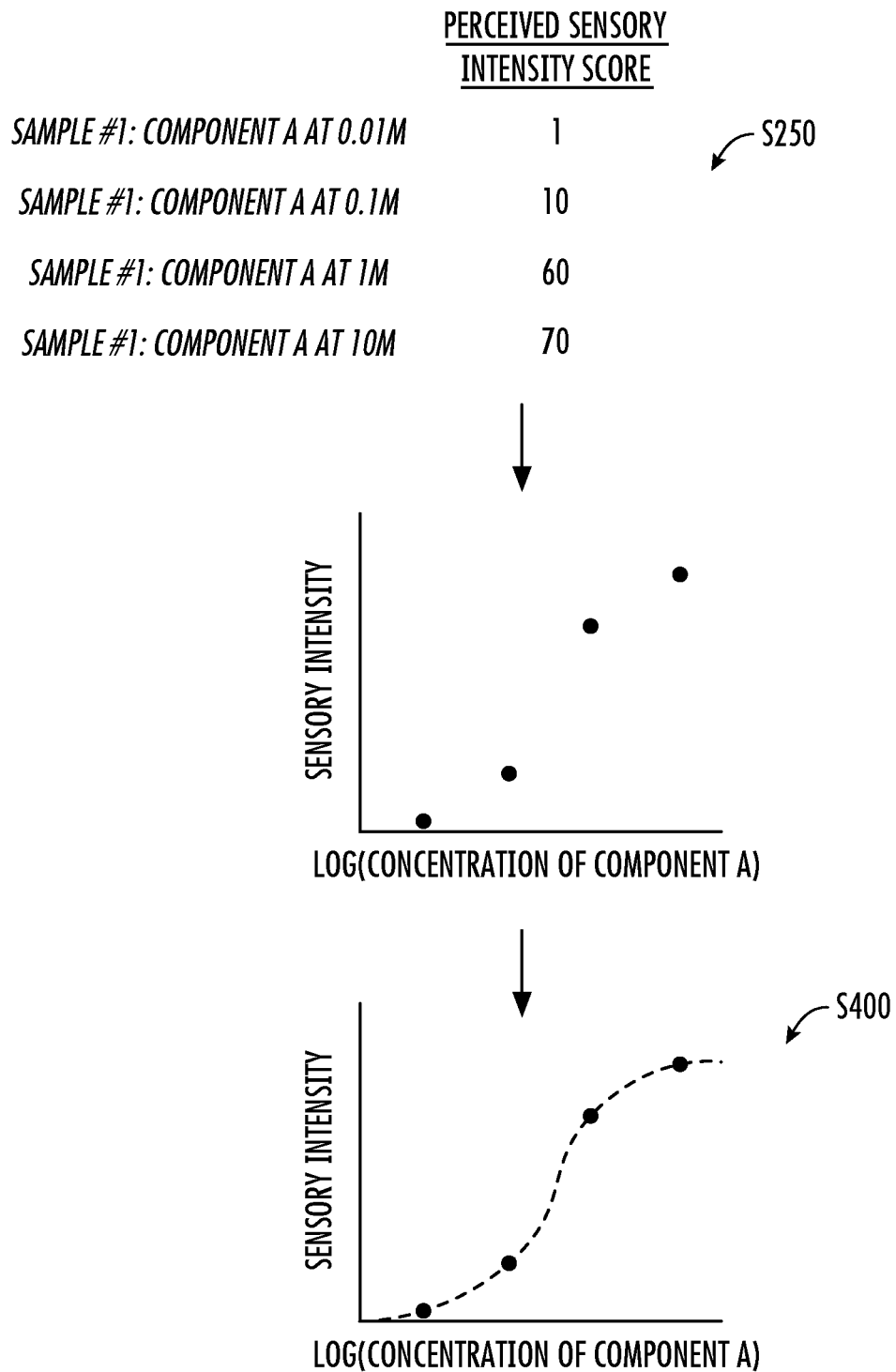
FIG. 4 depicts an illustrative example of determining a sensory function.

In a second example, S400 can include training a first model in the component model to learn an initial sensory function (e.g., an initial set of sensory function parameters), and training a second model in the component model to output sensory function parameter adjustments based on context and/or any other sample attributes. In a specific example, S200 and/or S250 can be performed for a set of samples containing the same component at differing concentrations to determine a sensory characterization (e.g., perceived sensory intensity score) for each given concentration, which can be used to learn the initial sensory function (sensory characterization versus component concentration). In an illustrative example, the sensory data for the set of single-component samples can be fit to a Hill equation model. An example is shown in FIG. 4. In another specific example, the second model in the component model can learn sensory function parameter adjustments using partial pooling methods (e.g., wherein learn context parameters such as sensory panelist and/or matrix parameters are constrained based on the population parameters), using Bayesian methods, and/or any other learning methods.

In this variant, training the mixture model to output a sensory characterization based on outputs from the component model (e.g., component sensory characterizations, sensory functions/sensory function parameters, etc.) and/or sample attributes can be performed using methods described in the first variant (e.g., using the training targets and/or comparisons described in the first variant). Examples are shown in FIG. 7A, FIG. 7C, FIG. 7D, FIG. 7E, FIG. 10A, and FIG. 10B.

In a first illustrative example, a model (e.g., a component model) can be trained to predict a sensory function for a sample or component thereof based on the sample attributes by: determining a first value for a sensory characteristic (e.g., sensory intensity, quality, etc.) for a first sample; using the model, predicting a sensory function for a second sample or component thereof based on the second sample's attributes; determining a second value for the sensory characteristic from the sensory function; determining a predicted ranking between the first and second samples based on the first and second values, comparing the predicted ranking with an actual ranking between the first and second samples (e.g., from S200); then training or updating the model based on the comparison.

In a second illustrative example, a component model and/or a mixture model can be trained to predict a sensory characterization for a sample by: determining a first value for a sensory characteristic for a first sample; using the component model, predicting a sensory function for each component of a second sample based on the second sample's attributes; for each component of the second sample, determining a component value for the sensory characteristic from the respective sensory function; using the mixture model, determining a second value for the sensory characteristic based on the component values; determining a predicted ranking between the first and second samples based on the first and second values, comparing the predicted ranking with an actual ranking between the first and second samples (e.g., from S200); then training or updating the component model and/or mixture model based on the comparison.

In a third illustrative example, a model can be trained to predict the rating for a sample by: predicting a rating value based on the sample attributes for a sample, comparing the predicted rating value with an actual rating value (e.g., calculated from the rankings in S200), and training or updating the model based on the comparison. The ratings can be for one or more sensory characteristics (e.g., flavors, odors, intensity, etc.). The ratings can be used to determine how similar the sample is to a target food (e.g., dairy product) being replicated, or be otherwise used.

In a fourth illustrative example, a model can be trained to predict the sensory characteristics (e.g., flavors, odors, etc.) based on the sample attributes for a sample, wherein the training targets can be the sensory characteristic values determined by the sensory panelist from S200. This model can be an autoencoder (e.g., configured to encode the attribute values into a latent space and decode the encoded attribute values into the sensory characteristic values), a classifier, and/or any other suitable model.

In a fifth illustrative example, a model can be trained to predict the sensory characterization for a sample by: predicting a sensory characterization for each of a set of training samples using the model; determining a predicted sensory ranking for the set of training samples based on the predicted sensory characterizations; and training or updating the model based on a comparison between the predicted flavor ranking and a panelist sensory ranking (e.g., determined in S200).

However, the sensory characterization model can be otherwise trained.

Determining attributes for a test sample S500 functions to determine a set of sensory characterization model inputs for a test sample (e.g., without associated sensory data from S200, not previously compared to a specific target sample, etc.). S500 can be performed after S400 and/or at any other time.

In variants, S500 can include determining attributes of the test sample as described in S100. In a first example, S500 can include measuring attributes of the test sample. In a second example, S500 can include predicting attributes of the test sample using an attribute prediction model (e.g., trained on previous samples with measured attributes). In a third example, S500 can include predicting attributes of the test sample using the sensory characterization model (e.g., via S600, predicting sample attributes that would generate a target sensory characterization, etc.). In a fourth example, S500 can include randomly determining test sample attributes (e.g., randomly determining different component values). In a fifth example, S500 can include using Bayesian optimization to determine the set of sample attributes for a subsequent test sample based on the results (e.g., similarity to a target product, such as a dairy replacement) of a prior test sample. In a specific example, explainability and/or interpretability methods can be used with the sensory characterization model to determine influential attributes, wherein the influential attributes are adjusted to increase a similarity between sensory characterization for the test sample and a target sensory characterization.

However, test sample attributes can be otherwise determined.

Determining a sensory characterization for the test sample S600 functions to determine (e.g., predict, infer, look up, estimate, calculate, etc.) sample sensory characterizations, sensory data, and/or sensory scores; predict sensory similarity between two or more samples; determine a new sample (e.g., new sample attributes) with a target sensory characterization; determine impurities present in a sample; determine an uncertainty parameter for a sensory characterization; and/or determine any other suitable information. S600 can be performed after S500, after S400, during S400, and/or any other time.

Figure 11:
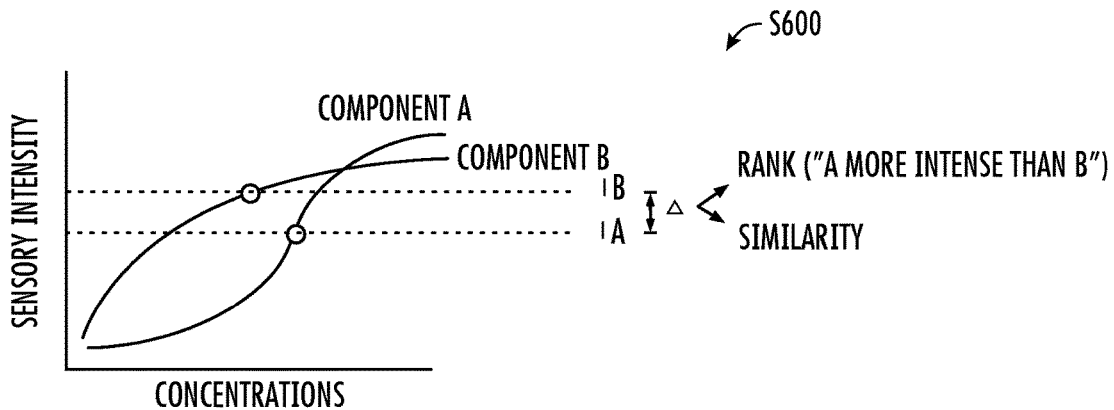
FIG. 11 depicts sensory functions for two components and downstream analyses (e.g., relative ranking probability distribution, similarity score, etc.) that can be derived from the curves.

Determining the sensory characterization can include using the sensory characterization model (e.g., the trained sensory characterization model) to determine a sensory characterization (e.g., predicted sensory characterization) for a test sample based on the attributes for the test sample (e.g., from S500). Example shown in FIG. 11.

In a first variant, the determined sensory characterization can be used for sensory characterization determination for a new, untested sample (e.g., without associated sensory data from S200, not previously compared to a specific target sample, etc.). For example, the sensory characterization can be of the same form as scores from S250 (e.g., such that the sensory characterization can be subsequently validated using S250). In a first specific example, S600 can include determining a rating for the test sample given the test sample attributes. The test sample rating can be compared against a rating for the target product (e.g., dairy replacement; determined using the same model), wherein the test sample can be considered an adequate replacement for the target product when the respective ratings are substantially similar (e.g., less than a predetermined threshold difference). Alternatively, the rating can be otherwise used. In a second specific example, S600 can include determining a ranking for the test sample (e.g., relative to the set of training samples or the set of S200 samples) given the test sample attributes. The test sample can be considered an adequate replacement for the target product when the respective rankings are substantially similar, and/or the rankings can be otherwise used. In a third specific example, S600 can include determining a sensory function for given the test sample attributes. The test sample can be considered an adequate replacement for the target product when the sensory values determined from the sensory function are substantially similar to the target product's sensory values, and/or the sensory function can be otherwise used. In a fourth specific example, the sensory characterization is predicted based on test sample context, wherein the context includes a sensory panelist (e.g., attributes for a sensory panelist). In this example, the sensory characterization is a predicted sensory characterization corresponding to sensory data (e.g., a ranking and/or rating) that the sensory panelist would report for the test sample. The sensory panelist can be a sensory panelist used in S200, a new sensory panelist, a representative sensory panelist, and/or any other sensory panelist. For example, each sensory panelist in S200 can be associated with a set of parameters (e.g., a parameterized sensory panelist, parameters associated with adjustments to the sensory function based on the sensory panelist, nonsemantic parameters, semantic parameters, etc.), wherein the parameters are determined based on the associated S200 and/or S250 data. The representative sensory panelist can be defined by aggregate parameters determined based on the individual S200 sensory panelist parameters. The aggregate parameters can be median, average, any other statistical measure, parameters determined using a model, and/or otherwise determined.

Figure 9:
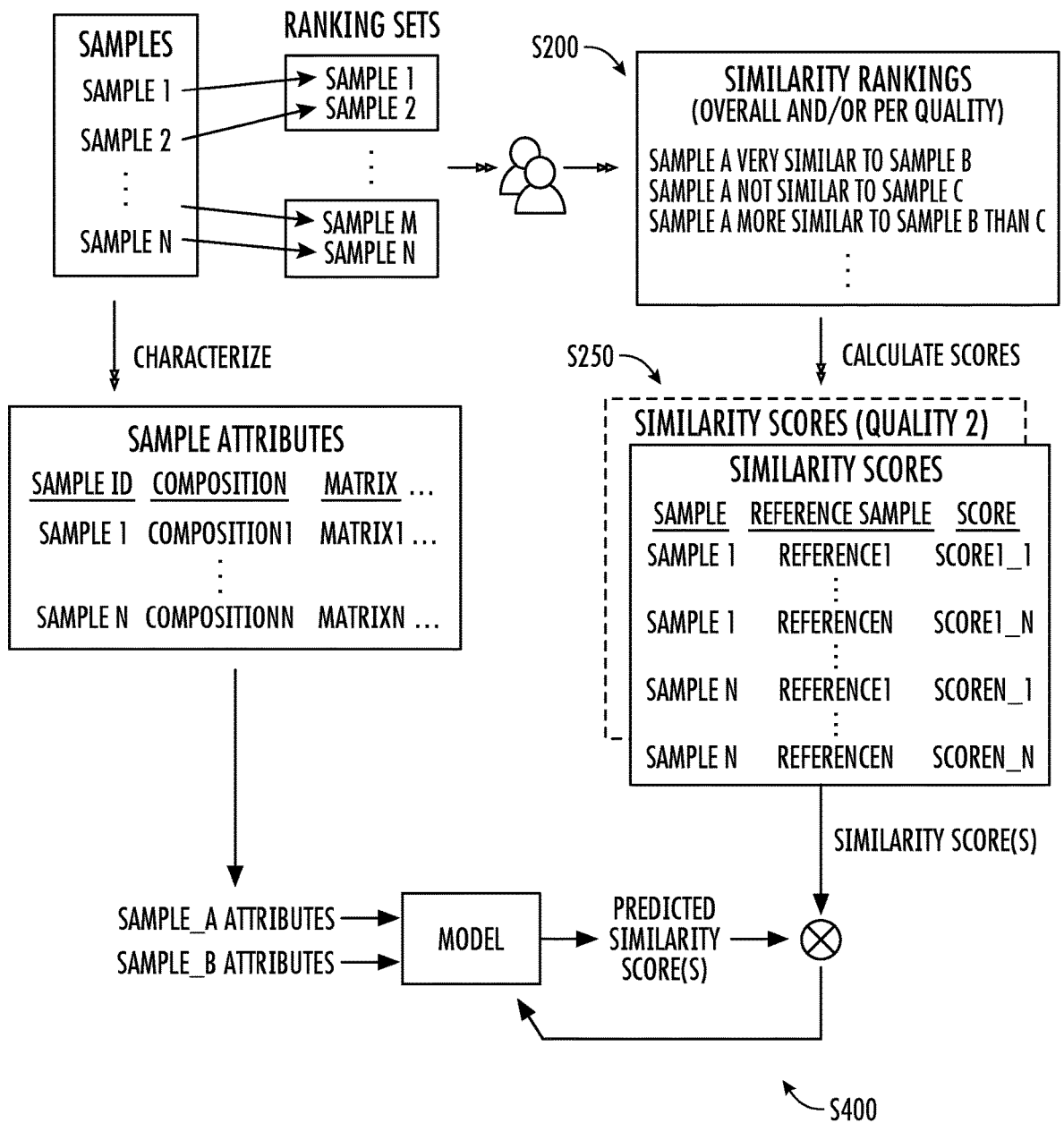
FIG. 9 depicts an example of validating the sensory similarity between a set of samples.
Figure 10A:
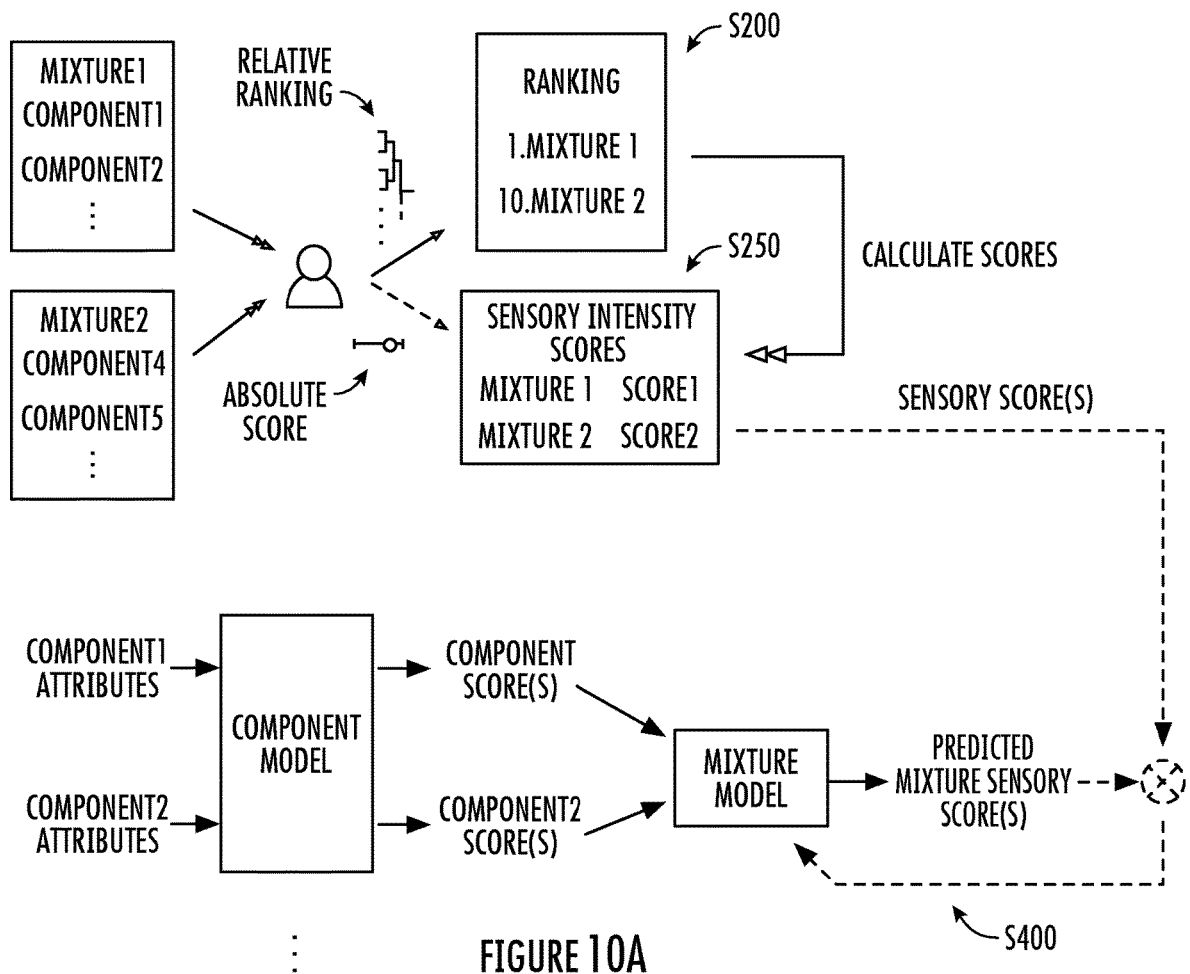
FIGS. 10A and 10B depict examples of predicting sensory characterizations (e.g., sensory intensities) for a mixture of compositions.
Figure 10B:
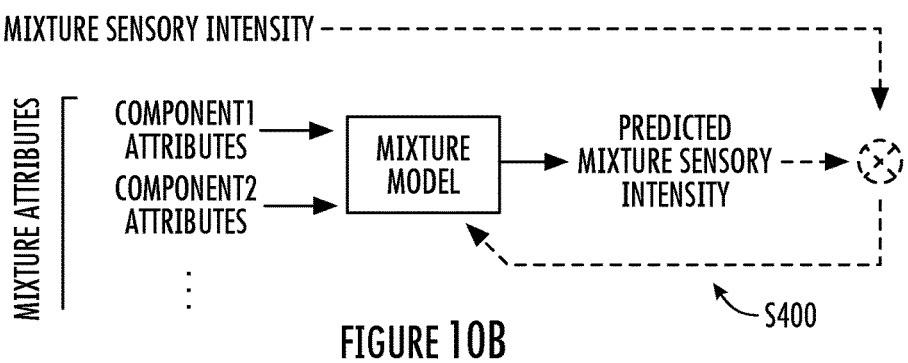

In a second variant, the determined sensory characterization can be used for sensory similarity evaluation (e.g., a sensory similarity score). The evaluation can be performed using sensory characterizations and/or components of sensory characterizations (e.g., a sensory characterization vector projected into a subspace, for a specific sensory quality, etc.). In a first embodiment, a comparison between the predicted sensory characterization of a prototype sample and the sensory characterization of a target sample (e.g., predicted and/or otherwise determined) can be used to determine the sensory similarity score (e.g., the degree of sensory intensity and/or sensory quality similarity). The comparison can be a distance-based comparison (e.g., Chi-square, Euclidean distance, Mahalanobis distance, Manhattan distance, Wasserstein distance etc.), angle comparison (e.g., cosine similarity), a correlation-based comparison (e.g., Pearson, Spearman, Kendall weighted and/or unweighted, etc.), and/or any other comparison and/or combination thereof. In a second embodiment, the sensory similarity score can be determined using a model trained to output a similarity score based on sensory characterizations and/or components of sensory characterizations (example shown in FIG. 9). In a third embodiment, a model can be trained to determine a similarity classification (e.g., similar, dissimilar, etc.) between different samples (e.g., based on the sample attributes, based on the sample intensity scores, etc.). In this variant, the sensory similarity score can be validated using a sensory panel (e.g., S200), which can optionally provide feedback to a sensory characterization model and/or a sensory similarity score model.

In a third variant, the determined sensory characterization can be used to determine a new sample (e.g., new sample attributes). In a first example, S600 can include perturbing attributes of a new sample (e.g., changing the process parameters) and/or predicting optimal adjustments to the attributes of a prototype sample (e.g., increasing the concentration of a specific sample component) to increase the sensory characterization similarity to a target sample. In a second example, attributes are selected to reduce uncertainty of a model, when a sample with the selected attributes is evaluated (e.g., in S200). In a third example, the sample attributes are determined using Bayesian optimization (e.g., wherein the surrogate function determines the sensory characteristic based on the sample attributes, and the next sample's attributes are determined using an acquisition function applied to the surrogate function). However, the sample attributes can be otherwise determined. The adjusted prototype can be manufactured and subsequently compared to the target sample to provide additional model feedback (e.g., S400).

However, the sensory characterization can be otherwise predicted.

The method can optionally include determining interpretability and/or explainability of one or more models (e.g., attribute prediction model, sensory characterization model, etc.), which can be used to identify errors in the data, identify ways of improving the model, reduce feature space, increase computational efficiency, determine influential features and/or values thereof, determine influential attributes and/or values thereof, determine influential sensory characteristics and/or values thereof, and/or otherwise used. For example, the method can determine which components contribute to a given sensory characteristic, and/or which components do not contribute to a given sensory characteristic (e.g., the model can learn to ignore alcohols). Interpretability and/or explainability methods can include: local interpretable model-agnostic explanations (LIME), Shapley Additive explanations (SHAP), Ancors, DeepLift, Layer-Wise Relevance Propagation, contrastive explanations method (CEM), counterfactual explanation, Protodash, Permutation importance (PIMP), L2X, partial dependence plots (PDPs), individual conditional expectation (ICE) plots, accumulated local effect (ALE) plots, Local Interpretable Visual Explanations (LIVE), breakDown, ProfWeight, Supersparse Linear Integer Models (SLIM), generalized additive models with pairwise interactions (GA2Ms), Boolean Rule Column Generation, Generalized Linear Rule Models, Teaching Explanations for Decisions (TED), and/or any other suitable method and/or approach.

5. Illustrative Examples

In a first illustrative example, a component model is trained to output a sensory function (e.g., sensory function parameters) for each sample component based on the respective sample component and associated sample attributes (e.g., sample context). The individual sensory functions (e.g., sigmoid curves) can be learned for each sample component (e.g., based on perceived sensory intensity data at different concentrations of the component, based on relative perceived sensory intensity data at different concentrations, etc.) to predict the sensory intensity at different concentrations (e.g., using a regression). The sensory functions and/or the component sensory characterizations determined based on the sensory functions can be used as input to a mixture model and/or as part of a mixture model that can output predicted sensory characterizations of different mixtures of the components (e.g., based on sensory intensity information at different mixture ratios and/or concentrations). In this example, the prediction of a sensory characterization for a mixture sample can include: measuring and/or predicting individual concentrations of each component in the sample; determining a sample context (e.g., sample manufacturing process parameters, sample matrix, a sensory panelist, etc.); predicting individual sensory characterizations for each component using the component model; and predicting a sample mixture sensory characterizations using the mixture model. The sensory functions can be learned and/or the model predicting the sensory functions can be trained by determining a relative ranking between a first and second sample component determined based on the respective sensory intensities (e.g., determined using the respective sensory functions), and determining whether the determined relative ranking is consistent with (e.g., matches) a manually-assigned relative ranking (e.g., from a sensory panelist).

In a second illustrative example, a single model is trained to predict a sensory characterization (e.g., including overall intensity, intensity for each sensory quality, sensory quality, etc.) for samples of component mixtures. The model input can be a matrix with entries for all components of interest (e.g., components missing from a test sample can be assigned a null or 0 value), and/or be otherwise configured. The model can be trained on sensory data including perceived sensory intensities of single-component samples and mixture samples. The model can be trained by determining a relative ranking (e.g., a probability for a relative ranking) between a first mixture sample and second mixture sample using the model, and comparing the determined relative ranking to a manually-assigned relative ranking (e.g., from a sensory panelist).

In a third illustrative example, the method can include: training a sensory model using a panelist sensory ranking for a set of training samples collected using a set of sensory panelists; determining attributes for a sample; and determining a sensory characterization for the sample based on the attributes using the trained sensory model. In specific examples, this example can be used in combination with any variants of the aforementioned processes discussed above.

In a fourth illustrative example, the method can include: determining a composition for a sample; learning a sensory function using sensory training data collected from set of sensory panelists; and determining a sensory characterization for the sample based on the sensory function and the composition. In specific examples, this example can be used in combination with any variants of the aforementioned processes discussed above.

Alternative embodiments implement the above methods and/or processing modules in non-transitory computer-readable media, storing computer-readable instructions that, when executed by a processing system, cause the processing system to perform the method(s) discussed herein. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. A method, comprising:
   training a flavor model using a panelist flavor ranking for a set of training samples collected using a set of sensory panelists;
   determining attributes for a sample; and
   determining a flavor characterization for the sample based on the attributes using the trained flavor model.

2. The method of claim 1, wherein training the flavor model comprises:
   predicting a flavor characterization for each of the set of training samples using the flavor model;
   determining a predicted flavor ranking for the set of training samples based on the predicted flavor characterizations; and
   training the flavor model based on a comparison between the predicted flavor ranking and the panelist flavor ranking.

3. The method of claim 2, wherein the predicted flavor ranking comprises a probability of a flavor ranking.

4. The method of claim 1, wherein the panelist flavor ranking comprises an intensity ranking for each of a set of flavor qualities for each of the set of training samples.

5. The method of claim 4, wherein the intensity ranking for a training sample is: higher than another sample, lower than another sample, or similar to another sample.

6. The method of claim 1, wherein the sample comprises a mixture of sample components, wherein determining the flavor characterization for the sample comprises:
   determining a component flavor characterization for each sample component;
   aggregating the component flavor characterizations to determine the flavor characterization for the sample.

7. The method of claim 6, wherein the trained flavor model comprises a component model and a mixture model, wherein the component model is used to determine the component flavor characterization for each sample component, and wherein the mixture model is used to aggregate the component flavor characterizations.

8. The method of claim 1, wherein the attributes comprise a context for the sample, wherein the context comprises at least one of a sensory panelist, a sample matrix, or environmental parameters.

9. The method of claim 1, wherein the sample comprises a mixture of sample components, wherein the attributes comprise a molecular structure for each sample component.

* * * * *